(12) United States Patent
Izutsu et al.

(10) Patent No.: US 6,834,532 B2
(45) Date of Patent: Dec. 28, 2004

(54) METHOD OF MEASURING GAS TRANSMISSION RATE OF PLASTIC FILM AND MEASURING APPARATUS AND COMPUTER PROGRAM PRODUCT USED THEREFOR

(75) Inventors: Naoki Izutsu, Sagamihara (JP); Nobuyuki Yajima, Sagamihara (JP)

(73) Assignee: Japan Aerospace Exploration Agency, an Independent Administrative Institution, Tokyo (JP)

( * ) Notice: Subject to any disclaimer, the term of this patent is extended or adjusted under 35 U.S.C. 154(b) by 0 days.

(21) Appl. No.: 10/429,874

(22) Filed: May 6, 2003

(65) Prior Publication Data
US 2004/0025571 A1 Feb. 12, 2004

(30) Foreign Application Priority Data
Aug. 6, 2002 (JP) .................................... 2002-228473

(51) Int. Cl.[7] .......................................... G01N 15/08
(52) U.S. Cl. ............................................... 73/38
(58) Field of Search ............................................... 73/38

(56) References Cited

U.S. PATENT DOCUMENTS

| | | | |
|---|---|---|---|
| 3,590,634 A | 7/1971 | Pasternak et al. ............. | 73/38 |
| 4,464,927 A | 8/1984 | Reid ............................. | 73/38 |
| 4,918,981 A * | 4/1990 | Gore ............................. | 73/76 |
| 5,107,696 A | 4/1992 | Mayer et al. ................... | 73/38 |
| 5,983,708 A * | 11/1999 | Mayer et al. ................... | 73/38 |
| 6,477,888 B1 * | 11/2002 | Mizobe ........................... | 73/38 |
| 6,487,891 B2 * | 12/2002 | Moretti .......................... | 73/38 |

OTHER PUBLICATIONS

Toshio Inoue, et al., "Changes in Oxygen Concentration and Volume of Gas Replaced Plastic Pouches During Storage", Japan Packaging Research, Package Study, vol. 11, No. 1, 1990, pp. 21–27.
Document Technical Information Association Homepage Seminar data, Text Sample T 11103 "High Barrier Film, Lecture 1", downloaded and printed on Jan. 9, 2002, url.http://www.gijutu.co.jp/doc/cc/111031.htm.

* cited by examiner

*Primary Examiner*—Daniel S. Larkin
(74) *Attorney, Agent, or Firm*—Oblon, Spivak, McClelland, Maier & Neustadt, P.C.

(57) ABSTRACT

A gas X is sealed into a test film bag, which is obtained by processing a test plastic film into a bag, and has a known mass and surface area. The mass of the test film bag in which the gas is sealed is measured by an electronic balance a plurality of numbers of times on the time series while the temperature is kept constant in a constant temperature vessel which is filled with a gas Y different from the gas X so as to make the pressure in the vessel equal to the internal pressure of the test film bag. A transmission rate associated with the gas X is then computed from the relationship between the measurement results, the mass of the test film bag alone, and the surface area by a computer.

18 Claims, 13 Drawing Sheets

State 0  Time $t_0$

State 1  Time $t_1$

State 2  Time $t_2$

State 3  Time $t_3$

US 6,834,532 B2

METHOD OF MEASURING GAS TRANSMISSION RATE OF PLASTIC FILM AND MEASURING APPARATUS AND COMPUTER PROGRAM PRODUCT USED THEREFOR

CROSS-REFERENCE TO RELATED APPLICATIONS

This application is based upon and claims the benefit of priority from the prior Japanese Patent Application No. 2002-228473, filed Aug. 6, 2002, the entire contents of which are incorporated herein by reference.

BACKGROUND OF THE INVENTION

1. Field of the Invention

The present invention relates to a method of measuring the gas transmission rate of a plastic film and a measuring apparatus for the method, which measure the transmission rates of various gases which are transmitted through plastic films.

2. Description of the Related Art

Plastic films have been used in a wide range of applications including food storage containers, and new materials for such films have been developed one after another. Gas permeability is an important property in understanding the performance and quality of these films, and hence measuring apparatuses based on various schemes have been developed and commercialized in various countries.

There are three known methods of measuring gas transmission rates for general gases: the differential pressure method, the isobaric method, and the small bag method. For water vapor, the cap method, the moisture sensor method, the infrared sensor method, and the dish method are known.

The gas transmission rates of films are general measured by using the differential pressure method or the isobaric method defined in JIS (Japanese Industrial Standard) (Testing method for gas transmission rate through plastic film and sheeting: JIS K 7126, testing methods for water vapor transmission rate of plastic film and sheeting; JIS K 7129, method of permeability test for moisture proof packing case; and JIS Z 02222, and testing methods for determination of the water vapor transmission rate of moisture-proof packaging materials: JIS Z 0208).

In the differential pressure method, one of the two portions separated by a test piece is kept in a vacuum, and a test gas is introduced into the other portion, thereby obtaining a gas transmission rate on the basis of an increase in pressure on the low-pressure side. In the isobaric method, a test gas is supplied to one of the two portions separated by a test piece while a carrier gas is flowed in the other portion at equal pressure, and the amount of gas transmitted is measured by some kind of gas detector or gas chromatograph. Measuring apparatuses based on the differential pressure method and the isobaric method have been developed and commercialized for a long time. In either of the methods, the surrounding of a test piece attached to a measuring portion must completely be sealed, and measuring apparatuses themselves are complicated.

The measuring method based on the small bag method was made public (Toshio Inoue and Takasuke Ishitani, "Changes in Oxygen Concentration and Volume over Time in Gas Purge Packaging", Packaging Study Vol. 11, No. 1 (1990), pp. 21–27). According to this method, a change in gas concentration in the bag and a change in the volume of the bag are checked. When a film subjected to gas transmission rate measurement is to be actually used as a product, the film is often processed into a bag-like airtight container and, for example, food is sealed into the container. The small bag method allows tests and evaluations in accordance with actual usage including the structures of bags, and hence is considered to have a wide range of applications.

In this method, however, both a change in gas concentration and a change in bag volume must be measured. A volume change is obtained from, for example, an increase in water level upon sinking a bag into the water, whereas a concentration change is obtained by using, for example, a gas chromatograph. There is therefore no merit in directly measuring an airtight bag, and no measuring apparatus based on this method has been commercialized.

Either of the cap method and the dish method which use no gas sensor is a method of measuring an increase in the weight of a hygroscopic material due to water vapor that is transmitted into a container or bag; measurement is limited to water vapor.

As described above, the conventional methods of measuring the gas transmission rates of plastic films demand complicated procedures and complicated measuring apparatuses.

BRIEF SUMMARY OF THE INVENTION

The present invention has been made in consideration of the above situation, and has as its object to provide a method of measuring the gas transmission rate of a plastic film, which requires only simple measurement preparations and procedures and exhibits very high measurement precision as compared with the conventional techniques, a measuring apparatus used for the measuring method, and a gas transmission rate measuring program using the measuring method.

In order to achieve the above object, according to the present invention, there is provided a method of measuring a gas transmission rate of a plastic film, comprising sealing a gas X into a test film bag which is formed by processing a test plastic film into a bag and has a known mass and surface area, measuring a mass of the test film bag in which the gas is sealed, a plurality of numbers of times on the time series, while keeping a temperature constant in a temperature-controlled airtight vessel which is filled with a gas Y different from the gas X so as to make a pressure in the vessel equal to an internal pressure of the test film bag, and obtaining a transmission rate (a value representing the number of moles of a gas transmitted through a test piece with a unit area in a unit time at a unit partial pressure difference) associated with the gas X from a relationship between the measurement results, the mass of the test film bag alone, and the surface area.

More specifically, this method is executed by program processing by an arithmetic processing apparatus on the basis of the following techniques:

(1) A method of measuring a gas transmission rate of a plastic film, in which when a transmission rate (a value representing the number of moles of a gas transmitted through a test piece with a unit area in a unit time at a unit partial pressure difference) $k_x$ [mol/m²sPa] of a gas X is known, a transmission rate $k_y$ [mol/m²sPa] of a gas Y through a test plastic film is measured, comprising:

preparing a test film bag by processing the test plastic film into a bag, and measuring a mass $m_f$ [kg] of the test film bag alone and a total surface area A [m²] associated with gas transmission in advance;

sealing the gas X into the test film bag at a density $\rho_x$, and measuring masses $m_0$ [kg], $m_1$ [kg], and $m_2$ [kg] of the test film bag in which the gas is sealed at least at times $t_0$ [s], $t_1$ [s], and $t_2$ [s] in an airtight vessel which is filled with the gas Y at a density $\rho_y$ so as to set a pressure P [Pa] equal to an internal pressure of the test film bag and in which a temperature is kept constant at a measurement temperature T [K];

obtaining volumes $V_{x0}$, $V_{x1}$, and $V_{x2}$ of the gas X in the test film bag at times $t_0$, $t_1$, and $t_2$ from $$V_{x0}=(m_0-m_f)/(\rho_x-\rho_y)$$

$$V_{x1}=(m_1-m_f)/(\rho_x-\rho_y)$$

$$V_{x2}=(m_2-m_f)/(\rho_x-\rho_y)$$

obtaining $\lambda_x$ by substituting the obtained results into the following equation for obtaining $\lambda_x$:

$$\lambda_x=\{a(t_1-t_0)-b(t_2-t_0)\}/(aV_{x1}-bV_{x2}-cV_{x0})$$

for $$a=\log V_{x0}-\log V_{x2}$$

$$b=\log V_{x0}-\log V_{x1}$$

$$c=\log V_{x1}-\log V_{x2}$$

and
computing $$k_y=(\lambda_x K_x^2+K_x)/(RTA)$$

where R is a gas constant and $K_x=k_x RTA$ thereby obtaining the transmission rate $k_y$ of the gas Y when the transmission rate $k_x$ is known.

(2) A method of measuring a gas transmission rate of a plastic film, in which when a transmission rate (a value representing the number of moles of a gas transmitted through a test piece with a unit area in a unit time at a unit partial pressure difference) $k_y$ [mol/m²sPa] of a gas Y is known, a transmission rate $k_x$ [mol/m²sPa] of a gas X through a test plastic film is measured, comprising:

preparing a test film bag by processing the test plastic film into a bag, and measuring a mass $m_f$ [kg] of the test film bag alone and a total surface area A [m²] associated with gas transmission in advance;

sealing the gas X into the test film bag at a density $\rho_x$, and measuring masses $m_0$ [kg], $m_1$ [kg], and $m_2$ [kg] of the test film bag in which the gas is sealed at least at times $t_0$ [s], $t_1$ [s], and $t_2$ [s] in an airtight vessel which is filled with the gas Y at a density $\rho_y$ so as to set a pressure P [Pa] equal to an internal pressure of the test film bag and in which a temperature is kept constant at a measurement temperature T [K];

obtaining volumes $V_{x0}$, $V_{x1}$, and $V_{x2}$ of the gas X in the test film bag at times $t_0$, $t_1$, and $t_2$ from $$V_{x0}=(m_0-m_f)/(\rho_x-\rho_y)$$

$$V_{x1}=(m_1-m_f)/(\rho_x-\rho_y)$$

$$V_{x2}=(m_2-m_f)/(\rho_x-\rho_y)$$

obtaining $\lambda_x$ by substituting the obtained results into the following equation for obtaining $\lambda_x$:

$$\lambda_x=\{a(t_1-t_0)-b(t_2-t_0)\}/(aV_{x1}-bV_{x2}-cV_{x0})$$

for $$a=\log V_{x0}-\log V_{x2}$$

$$b=\log V_{x0}-\log V_{x1}$$

$$c=\log V_{x1}-\log V_{x2}$$

and
when $\lambda_x>0$, computing $$k_x=\{-1+(1+4\lambda_x K_y)^{1/2}\}/(2\lambda_x RTA)$$

where R is a gas constant and $K_x=k_x RTA$
and when $\lambda_x<0$, computing $$k_x=\{-1\pm(1+4\lambda_x K_y)^{1/2}\}/(2\lambda_x RTA)$$

thereby obtaining the transmission rate $k_x$ of the gas X when the transmission rate $k_y$ is known.

(3) A method of measuring a gas transmission rate of a plastic film, in which when a transmission rate (a value representing the number of moles of a gas transmitted through a test piece with a unit area in a unit time at a unit partial pressure difference) $k_y$ [mol/m²sPa] of a gas Y is known, a transmission rate $k_x$ [mol/m²sPa] of a gas X through a test plastic film ($k_x \gg k_y$) is measured, comprising:

preparing a test film bag by processing the test plastic film into a bag, and measuring a mass $m_f$ [kg] of the test film bag alone and a total surface area A [m²] associated with gas transmission in advance;

sealing the gas X into the test film bag at a density $\rho_x$, and measuring masses $m_0$ [kg], $m_1$ [kg], and $m_2$ [kg] of the test film bag in which the gas is sealed at least at times $t_0$ [s], $t_1$ [s], and $t_2$ [s] in an airtight vessel which is filled with the gas Y at a density $\rho_y$ so as to set a pressure P [Pa] equal to an internal pressure of the test film bag and in which a temperature is kept constant at a measurement temperature T [K];

obtaining volumes $V_{x0}$, $V_{x1}$, and $V_{x2}$ of the gas X in the test film bag at times $t_0$, $t_1$, and $t_2$ from $$V_{x0}=(m_0-m_f)/(\rho_x-\rho_y)$$

$$V_{x1}=(m_1-m_f)/(\rho_x-\rho_y)$$

$$V_{x2}=(m_2-m_f)/(\rho_x-\rho_y)$$

obtaining $\lambda_x$ by substituting the obtained results into the following equation for obtaining $\lambda_x$:

$$\lambda_x=\{a(t_1-t_0)-b(t_2-t_0)\}/(aV_{x1}-bV_{x2}-cV_{x0})$$

for $$a=\log V_{x0}-\log V_{x2}$$

$$b=\log V_{x0}-\log V_{x1}$$

$$c=\log V_{x1}-\log V_{x2}$$

and
computing $$k_x=-1/(\lambda_x RTA)$$

where R is a gas constant
thereby approximating the transmission rate $k_x$ of the gas X when the transmission rate $k_y$ ($k_x \gg k_y$) is known.

(4) A method of measuring a gas transmission rate of a plastic film, in which when a transmission rate (a value representing the number of moles of a gas transmitted through a test piece with a unit area in a unit time at a unit partial pressure difference) $k_y$ [mol/m²sPa] of a gas Y is known, a transmission rate $k_x$ [mol/m²sPa] of a gas X through a test plastic film ($k_x \gg k_y$) is measured, comprising:

preparing a test film bag by processing the test plastic film into a bag, and measuring a mass $m_f$ [kg] of the test film bag alone and a total surface area A [m²] associated with gas transmission in advance;

sealing the gas X into the test film bag at a density $\rho_x$, and measuring masses $m_0$ [kg] and $m_1$ [kg] of the test film bag in which the gas is sealed at least at times $t_0$ [s] and $t_1$ [s] in an airtight vessel which is filled with the gas Y at a density $\rho_y$ so as to set a pressure P [Pa] equal to an internal pressure of the test film bag and in which a temperature is kept constant at a measurement temperature T [K];

obtaining volumes $V_{x0}$ and $V_{x1}$ of the gas X in the test film bag at times $t_0$ and $t_1$ from $$V_{x0}=(m_0-m_f)/(\rho_x-\rho_y)$$

$$V_{x1}=(m_1-m_f)/(\rho_x-\rho_y)$$

and
computing $$k_x=(V_{x1}-V_{x0})/\{(t_1-t_0)RTA\}$$

where R is a gas constant
thereby approximating the transmission rate $k_x$ of the gas X when the transmission rate $k_y$ ($k_x \gg k_y$) is known.

(5) A method of measuring a gas transmission rate of a plastic film, which measures a transmission rate (a value representing the number of moles of a gas transmitted through a test piece with a unit area in a unit time at a unit partial pressure difference) $k_x$ [mol/m²sPa] of a gas X and a transmission rate $k_y$ [mol/m²sPa] of a gas Y through a test plastic film, comprising:

preparing first and second test film bags each obtained by processing the test plastic film into a bag, and measuring masses $m_f$ [kg] and $m_f'$ [kg] of the respective test film bags alone and total surface areas A [m²] and A' [m²] associated with gas transmission in advance;

sealing the gas X into the first test film bag at a density $\rho_x$, and measuring masses $m_0$ [kg], $m_1$ [kg], and $m_2$ [kg] of the first test film bag in which the gas is sealed at least at times $t_0$ [s], $t_1$ [s], and $t_2$ [s] in an airtight vessel which is filled with the gas Y at a density $\rho_y$ so as to set a pressure P [Pa] equal to an internal pressure of the first test film bag and in which a temperature is kept constant at a measurement temperature T [K];

sealing the gas Y into the second test film bag at a density $\rho_y'$, and measuring masses $m_0'$ [kg], $m_1'$ [kg], and $m_2'$ [kg] of the second test film bag in which the gas is sealed at least at times $t_0'$ [s], $t_1'$ [s], and $t_2'$ [s] in an airtight vessel which is filled with the gas X at a density $\rho_x'$ so as to set a pressure P' [Pa] equal to an internal pressure of the second test film bag and in which a temperature is kept constant at a measurement temperature T' (T'=T) [K];

obtaining volumes $V_{x0}$, $V_{x1}$, and $V_{x2}$ of the gas X in the first test film bag at times $t_0$, $t_1$, and $t_2$ from $$V_{x0}=(m_0-m_f)/(\rho_x-\rho_y)$$

$$V_{x1}=(m_1-m_f)/(\rho_x-\rho_y)$$

$$V_{x2}=(m_2-m_f)/(\rho_x-\rho_y)$$

obtaining $\lambda_x$ by substituting the obtained results into the following equation for obtaining $\lambda_x$:

$$\lambda_x=\{a(t_1-t_0)-b(t_2-t_0)\}/(aV_{x1}-bV_{x2}-cV_{x0})$$

for $a=\log V_{x0}-\log V_{x2}$ $b=\log V_{x0}-\log V_{x1}$ $c=\log V_{x1}-\log V_{x2}$ obtaining volumes $V_{y0}'$, $V_{y1}'$, and $V_{y2}'$ of the gas Y in the first test film bag at times $t_0'$, $t_1'$, and $t_2'$ from $$V_{y0}'=(m_0'-m_f')/(\rho_y'-\rho_x')$$

$$V_{y1}'=(m_1'-m_f')/(\rho_y'-\rho_x')$$

$$V_{y2}'=(m_2'-m_f')/(\rho_y'-\rho_x')$$

obtaining $\lambda_y$ by substituting the obtained results into the following equation for obtaining $\lambda_y$:

$$\lambda_y=\{a'(t_1'-t_0')-b'(t_2'-t_0')\}/(a'V_{y1}'-b'V_{y2}'-c'V_{y0}')$$

for $a'=\log V_{y0}'-\log V_{y2}'$ $b'=\log V_{y0}'-\log V_{y1}'$ $c'=\log V_{y1}'-\log V_{y2}'$ when $\lambda_x>0$ and $\lambda_y<0$, computing $$k_x=-1/(\lambda_x RTA)+1/\{RT(-\lambda_x\lambda_y AA')^{1/2}\}$$

$$k_y=-1/(\lambda_y RTA')-1/\{RT(-\lambda_x\lambda_y AA')^{1/2}\}$$

where R is a gas constant
and
when $\lambda_x<0$ and $\lambda_y>0$, computing $$k_x=-1/(\lambda_x RTA)-1/\{RT(-\lambda_x\lambda_y AA')^{1/2}\}$$

$$k_y=-1/(\lambda_y RTA')+1/\{RT(-\lambda_x\lambda_y AA')^{1/2}\}$$

thereby obtaining the transmission rate $k_x$ of the gas X and the transmission rate $k_y$ of the gas Y.

(6) When a saturation vapor pressure of the gas X is lower than atmospheric pressure, the pressure in the airtight vessel is reduced to make a saturation vapor pressure in the test film bag become higher than the pressure in the airtight vessel.

(7) A method of measuring a gas transmission rate of a plastic film, which measures a transmission rate (a value representing the number of moles of a gas transmitted through a test piece with a unit area in a unit time at a unit partial pressure difference) $k_x$ of a gas X, through a test plastic film, whose saturation vapor pressure is lower than atmospheric pressure at room temperature, comprising:

preparing a test film bag by processing the test plastic film into a bag, and measuring a mass $m_f$ [kg] of the test film bag alone and a total surface area A [m²] associated with gas transmission in advance;

sealing the gas X into the test film bag while part of the gas is a liquid such that the vapor pressure is set in a saturate state, and allowing measurement of a mass of the test film bag in which the gas is sealed in an airtight vessel which is filled with a gas Y whose saturation vapor pressure is higher than atmospheric pressure at room temperature and in which a measurement temperature can be arbitrarily controlled;

measuring a mass $m_0$ [kg] of the test film bag in which the gas is sealed in state 0 in which an internal temperature of the airtight vessel is set to $T_0$ [K] and a pressure is set to $P_0$ [Pa] equal to atmospheric pressure (a saturation vapor pressure $P_{x0}$ [Pa] of the gas X, a density $\rho_x$ of the gas X, and a density $\rho_y$ of the gas Y);

measuring a mass $m_1$ [kg] of the test film bag in which the gas is sealed in state 1 in which an internal temperature of the airtight vessel is set to $T_1$ [K] (a pressure $P_1$ [Pa], a saturation vapor pressure $P_{x1}$ [Pa] of the gas X, a density $\rho_{x1}$ of the gas X, and a density $\rho_{y1}$ of the gas Y);

measuring a mass m2 [kg] of the test film bag in which the gas is sealed in state 2 after a lapse of a predetermined period of time t [s] since state 1 while the internal temperature $T_1$ [K] of the airtight vessel (the pressure $P_1$ [Pa], the saturation vapor pressure $P_{x1}$ [Pa] of the gas X, the density $\rho_{x1}$ of the gas X, and the density $\rho_{y1}$ of the gas Y) is maintained;

after measurement in state 2, measuring a mass $m_3$ [kg] of the test film bag in which the gas is sealed in state 3 in which the internal temperature of the airtight vessel is set to $T_3$ [K] (a pressure $P_3$ [Pa] and a saturation vapor pressure $P_{x3}$ [Pa]);

obtaining a total mass of the liquid and gas in the test film bag in state 1 from $$m_{x1}+\rho_{x1}V_{x1}=m_1-m_f+(m_0-m_1)(P_0/P_{x0}-1)/(P_0/P_{x0}-P_1/P_{x1})$$

obtaining the total mass of the liquid and gas in the test film bag in state 2 from $$m_{x2}+\rho_{x2}V_{x2}=m_3-m_f+(m_2-m_3)(P_1/P_{x2}-1)/(P_1/P_{x2}-P_3/P_{x3})$$

and obtaining the transmission rate $k_x$ of the gas X by substituting the computation results into the following equation and computing the equation:

$$k_x=\{(m_{x1}+\rho_{x1}V_{x1})-(m_{x2}+\rho_{x2}V_{x2})\}/(tP_xA)$$

(8) In measurement of the mass, a measured weight value is corrected on the basis of a gravitational acceleration at a measurement place.

A measuring apparatus used to execute the above measuring method comprises a constant temperature vessel which is used as the airtight vessel and includes internal temperature control means and gas filling means, an electronic balance which is mounted in the constant temperature vessel and measures a mass of a test film bag in which the gas is sealed, and an arithmetic processing unit in which an arithmetic processing program in any one of (1) to (7) is installed in advance and which obtains a transmission rate value of a test gas by inputting the measurement results.

The above measuring apparatus further comprises measurement automating means for acquiring a measured mass value at a predetermined time from the electronic balance by setting an internal temperature in the constant temperature vessel to a measurement temperature through the internal temperature control means.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a pat of the specification, illustrate presently preferred embodiments of the invention, and together with the general description given above and the detailed description of the preferred embodiments given below, serve to explain the principles of the invention.

DETAILED DESCRIPTION OF THE INVENTION

An embodiment of the present invention will be described in detail with reference to the views of the accompanying drawing.

Figure 1:
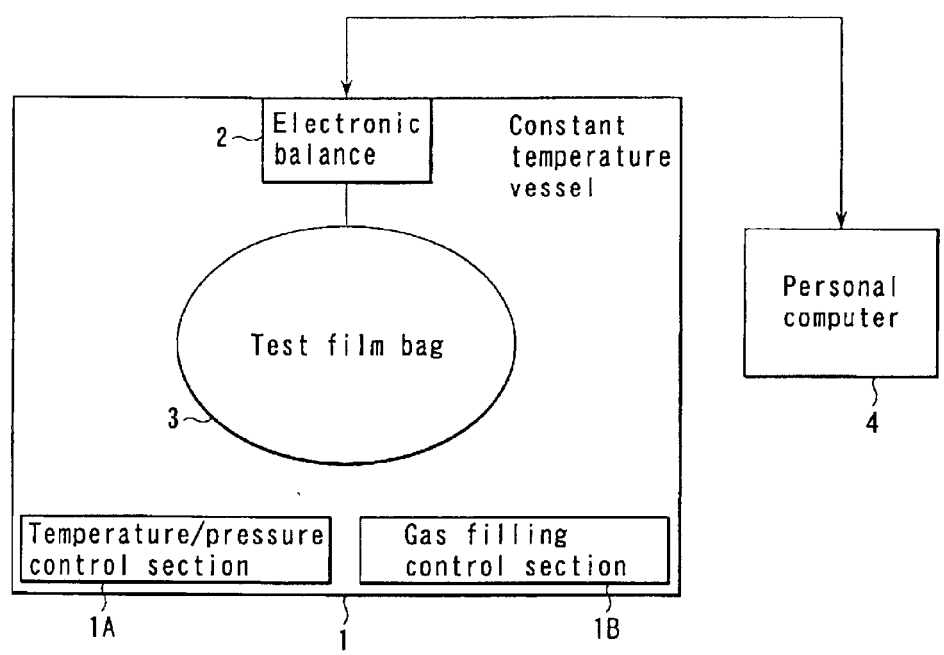
FIG. 1 is a schematic view showing the arrangement of a measuring apparatus used in a method of measuring the gas transmission rate of a plastic film according to an embodiment of the present invention.

FIG. 1 is a schematic view showing the arrangement of a measuring apparatus which is used to execute a method of measuring the gas transmission rate of a plastic film according to the present invention. Referring to FIG. 1, reference numeral 1 denotes a constant temperature vessel whose interior can be hermetically sealed. A precision electronic balance 2 is mounted in the constant temperature vessel 1. The constant temperature vessel 1 may have a structure in which a specimen is mounted on a base. If, however, the specimen is mounted on the base, part of the surface of the specimen cannot be used for the transmission of a gas, resulting in difficulty in calculating an effective surface area. It is therefore thought that higher measurement precision can be obtained by a scheme of keeping a specimen suspended to use its entire surface for the transmission of a gas. For this reason, in this embodiment, the electronic balance 2 of the suspension scheme is mounted on the inner upper surface of the constant temperature vessel 1 so that a specimen (a gas-sealed test film bag) 3 can be suspended from the suspension wire hook of the balance 2.

The constant temperature vessel 1 has a sufficiently large volume relative to the volume of the bag 3 and includes a temperature/pressure control section 1A for controlling the internal temperature and pressure to predetermined values and a gas filling control section 1B for filling the vessel 1 with a gas.

The electronic balance 2 is connected to a personal computer (PC) 4 through an interface (not shown). A program for measurement value acquisition/computation processing based on a measuring method of the present invention is installed in the PC 4 in advance. When this program is to be executed, a test start instruction is given after necessary data are input. With this operation, a mass at a predetermined time is measured from the electronic balance 2 and input to computational expressions, thus finally obtaining the gas transmission rate of the specimen 3.

A method of measuring the gas transmission rate of a plastic film by using the above measuring apparatus in a case wherein a general dry gas is used and the same method in a case wherein a gas whose saturation vapor pressure is lower than atmospheric pressure will be described separately.

(General Dry Gas)

Consider a case wherein a transmission rate (a value representing the number of moles of a gas transmitted through a test piece with a unit area in a unit time at a unit partial pressure difference) $k_x$ [mol/m²sPa] of a gas X through a plastic film having a given thickness and a transmission rate $k_y$ [mol/m²sPa] of a gas Y are simultaneously measured, and a case wherein the transmission rate $k_y$ is measured when the transmission rate $k_x$ is known. Assume that the gases X and Y are, for example, oxygen and nitrogen, respectively.

Figure 2:
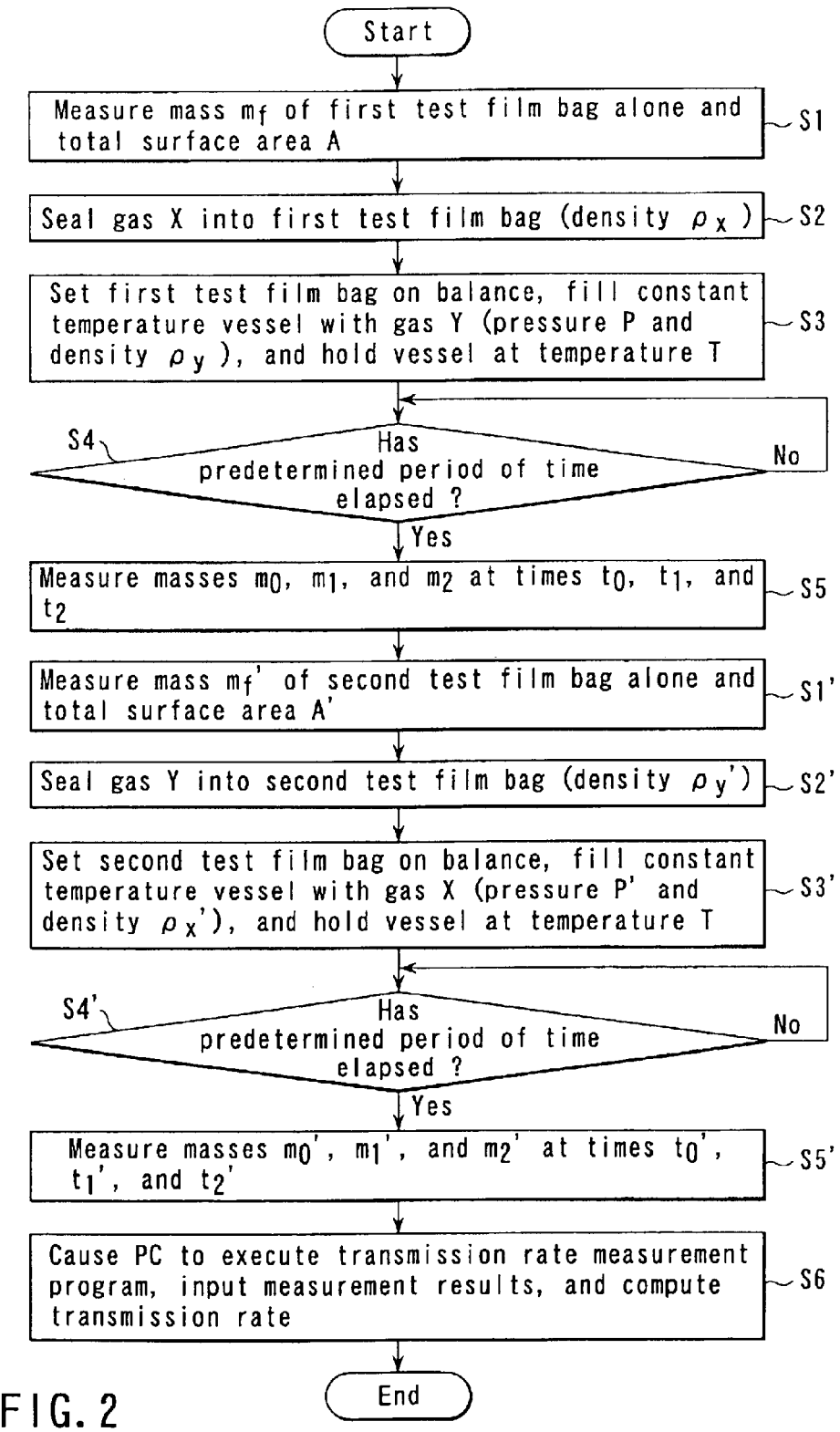
FIG. 2 is a flow chart showing the flow of measurement processing when a gas to be measured is a dry gas according to the first embodiment of the present invention.

First of all, the specimen (to be referred to as the test film bag hereinafter) 3 formed by processing a test film into a bag is prepared, and a mass $m_f$ [kg] of the bag alone and a total area A [m²] associated with the transmission of a gas are measured in advance (step S1), as shown in FIG. 2. The gas X is then charged into the test film bag 3 in a proper amount and the bag is sealed (density $\rho_x$ of the gas X) (step S2), as shown in FIG. 2. In this case, the gas Y may be mixed in the gas X. The amount of the gas X sealed is set to an amount at which no pressure acts on the bag 3 during the test under a test environmental temperature/pressure condition. That is, the internal pressure of the bag 3 is always kept equal to the pressure in the constant temperature vessel 1. the test film bag 3 in an amount sufficient to prevent portions of the inner surface of the test film bag 3 from coming into contact with each other. Alternatively, an unwoven fabric or structure that has no influence on this measurement may be inserted in the bag 3 to form a gap. In this case, care should be taken not to change the area of the surface through which the gas is transmitted and set a negative pressure in the bag 3 upon transmission of the gas.

Figure 3A:
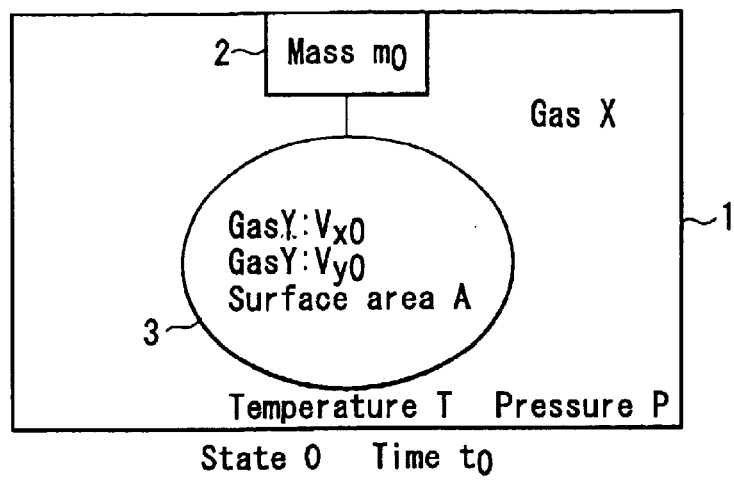
FIGS. 3A to 3F are conceptual views respectively showing set environments for states 0 to 2 and states 0' to 2' along the procedure in the first embodiment.

Subsequently, as shown in FIG. 3A, the gas-filled test film bag 3 is suspended from the electronic balance 2 mounted in the constant temperature vessel 1, and the constant temperature vessel 1 is filled with the gas Y alone and held at a measurement temperature T [K] (step S3). as shown in FIG. 2. At this time, the volume of the constant temperature vessel 1 is sufficiently larger than the volume of the bag 3, and the pressure in the constant temperature vessel 1 is always equal to atmospheric pressure.

After the above preparations are completed, the constant temperature vessel 1 is left standing for a proper period of time until the temperature in the constant temperature vessel 1 and the gas temperature in the test film bag 3 reach equilibrium and gas transmission reaches a steady state (step S4). as shown in FIG. 2. This also prevents a measurement error due to a time delay in gas transmission.

Figure 3B:
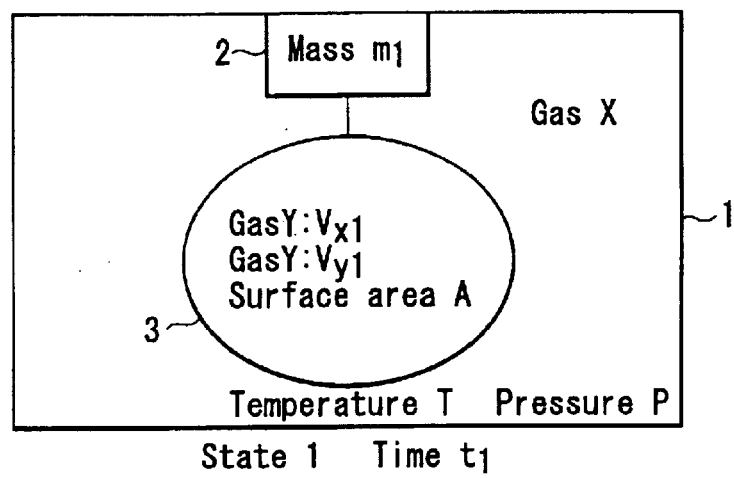
Figure 3C:
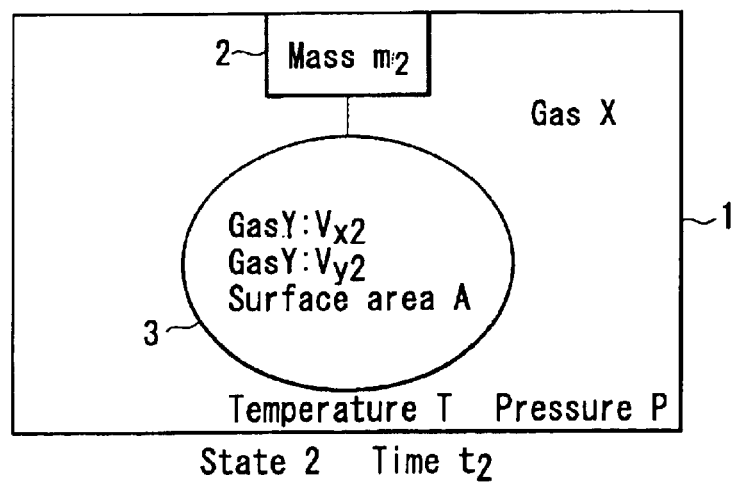

A mass ma [kg] of the gas-filled test film bag 3 is measured by the electronic balance 2 at measurement start time $t_0$ [s] (state 0: FIG. 3A). Masses $m_1$ [kg] and $m_2$ [kg] of the test film bag 3 are measured at proper time intervals, i.e., at time $t_1$ [s] (state 1: FIG. 3B) and time $t_2$ [s] (state 2: FIG. 3C) (step S5). as shown in FIG. 2. Assume that in this measurement, the difference between the gravitational accelerations at different measurement places has been corrected.

In this case, if the transmission rates of both the gases X and Y are unknown, the same processing as that in steps S1 to S5. as shown in FIG. 2, is performed upon interchanging the gases X and Y.

More specifically, in step S1', as shown in FIG. 2. a mass $m_r'$ [kg] of a second test film bag 3' alone an a total area A' [m²] are measured. In step S2', as shown in FIG. 2, the gas Y is sealed in the second test film bag 3' in a proper amount (density $\rho_y$ of the gas Y). In step S3', as shown in FIG. 2 the second test film bag 3' is suspended from the electronic balance 2, and the constant temperature vessel 1 is filled with the gas X alone (pressure P [Pa] and density $\rho_x$) and held at the measurement temperature T [K].

Figure 3D:
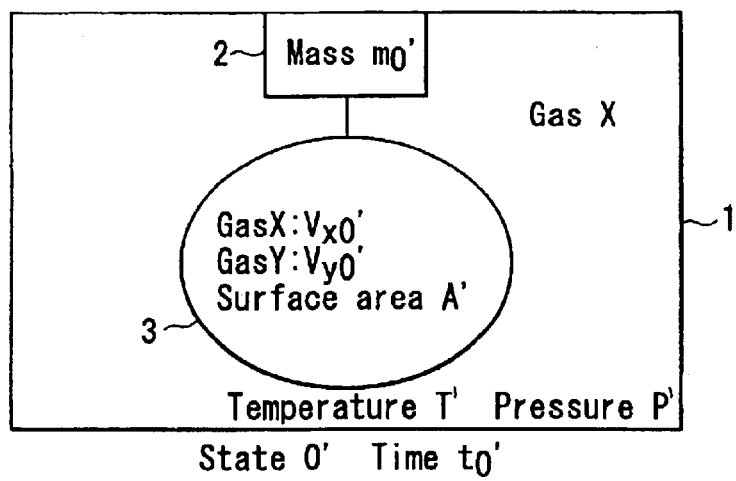
Figure 3E:
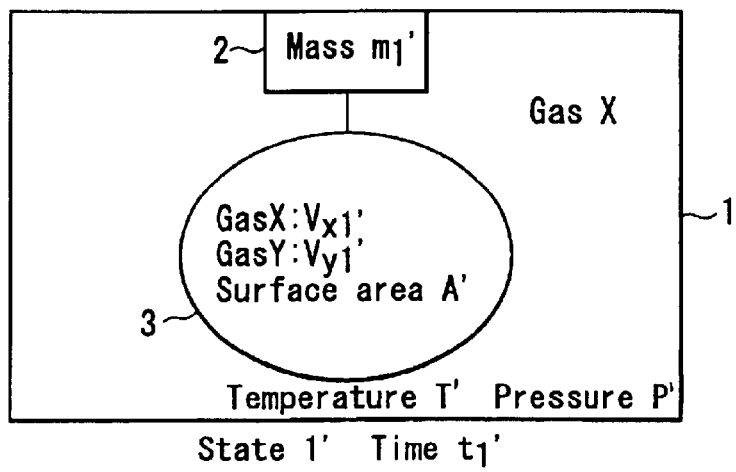
Figure 3F:
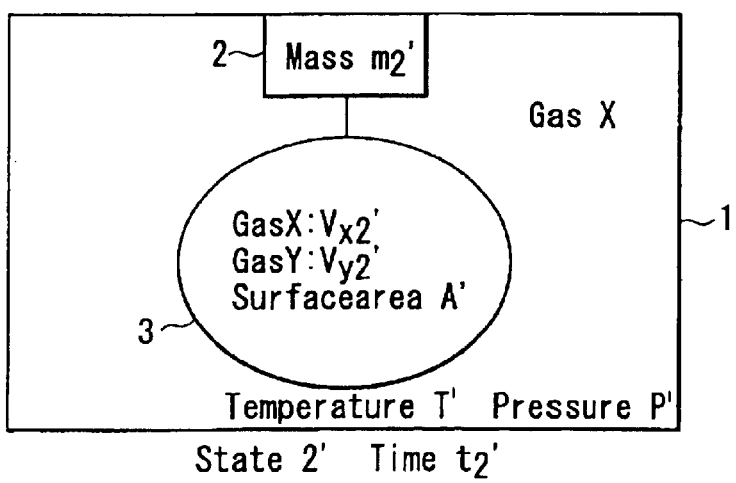

After the above preparations are completed, the constant temperature vessel 1 is left standing for a proper period of time until the temperature in the constant temperature vessel 1 and the gas temperature in the second test film bag 3' reach equilibrium and gas transmission reaches a steady state (step S4'), as shown in FIG. 2. Thereafter, in step S5', as shown in FIG. 2, masses $m_0'$ [kg], $m_1'$ [kg], and $m_2'$ [kg] of the second gas-filled test film bag 3' are measured by the electronic balance 2 at time $t_0'$ [s] (state 0': FIG. 3D), time $t_1'$ [s] (state 1': FIG. 3E), and time $t_2'$ [s] (state 2': FIG. 3F) (step S5'), as shown in FIG. 2. Assume that in this measurement as well, the difference between the gravitational accelerations at different measurement places has been corrected.

After the above measurement is completed, the personal computer 4 is made to execute a transmission rate measurement program to calculate the transmission rates of the gases X and Y by inputting the measurement results (step S6). With the above processing, the measurement procedure is completed.

Computational expressions for obtaining gas transmission rates from the above measurement values and predetermined values will be described below.

Let $\rho_x$ and $\rho_y$ be the densities of the gases X and Y in the bag 3 at the temperature T and pressure P, and $V_x$ and $V_y$ be the volumes of the gases X and Y. When the mass of the gas-filled bag 3 is measured in the constant temperature vessel 1, the mass of the gas Y flowing into the bag is canceled out by buoyancy according to the Archimedean principle, and the mass of the gas X exhibits a value proportional to the difference between the molecular weights of the two gases. This makes it possible to obtain only the volume $V_x$ of the gas X. Therefore, volumes $V_{x0}$, $V_{x1}$, and $V_{x2}$ of the gas X in the bag 3 at times $t_0$, $t_1$, and $t_2$ are given by $$V_{x0}=(m_0-m_f)/(\rho_x-\rho_y) \tag{1a}$$

$$V_{x1}=(m_1-m_f)/(\rho_x-\rho_y) \tag{1b}$$

$$V_{x2}=(m_2-m_f)/(\rho_x-\rho_y) \tag{1c}$$

The volumes $V_x$ and $V_y$ of the gas and the transmission rates $k_x$ and $k_y$ have the following relationship:

$$dV_x/dt=-K_xV_x/(V_x+V_y) \tag{2a}$$

$$dV_y/dt=-K_y\{V_y/(V_x+V_y)-1\} \tag{2b}$$

Letting R be a gas constant, $$K_x=k_xRTA \tag{3a}$$

$$K_y=k_yRTA \tag{3b}$$

According to equations (2a) and (2b), $$V_y - V_{y0} = -(K_y/K_x)(V_x - V_{x0}) \quad (4)$$

When equations (2a) and (2b) are solved for $V_x$, the following is obtained in the end:

$$t = \lambda_x V_x - C_1 \log V_x + C_2 \quad (5)$$

for $$\lambda_x = (K_y - K_x)/K_x^2 \quad (6)$$

Constants $C_1$, $C_2$, and $\lambda_x$ are determined from three sets of measurement values at different times $t_0$, $t_1$, and $t_2$. Of these constants, $\lambda_x$ is obtained by $$\lambda_x = \{a(t_1 - t_0) - b(t_2 - t_0)/(aV_{x1} - bV_{x2} - cV_{x0})\} \quad (7)$$

for $$a = \log V_{x0} - \log V_{x2} \quad (8a)$$

$$b = \log V_{x0} - \log V_{x1} \quad (8b)$$

$$c = \log V_{x1} - \log V_{x2} \quad (8c)$$

Solutions in the following six cases based on the correlation between the transmission rate $k_x$ of the gas X and the transmission rate $k_y$ of the gas Y will be described separately.

(1) When the transmission rate $k_x$ is known:
In this case, the transmission rate $k_y$ of the gas Y is obtained by $$k_y = (\lambda_x K_x^2 + K_x)/(RTA) \quad (9)$$

(2) When the transmission rate $k_y$ is known and $\lambda_x > 0$:
In this case, the transmission rate $k_x$ of the gas X is obtained by $$k_x = \{-1 + (1 + 4\lambda_x K_y)^{1/2}\}/(2\lambda_x RTA) \quad (10)$$

(3) When the transmission rate $k_y$ is known and $\lambda_x < 0$:
In this case, the transmission rate $k_x$ of the gas X is obtained by $$k_x = \{-1 \pm (1 + 4\lambda_x K_y)^{1/2}\}/(2\lambda_x RTA) \quad (11)$$

(4) When the transmission rate $k_y$ is known and $k_x \gg k_y$:
In this case, the transmission rate $k_x$ of the gas X is approximated by $$k_x = -1/(\lambda_x RTA) \quad (12)$$

(5) When the transmission rate $k_y$ is known, $k_x \gg k_y$, and only the gas X is sealed in the bag 3:
In this case, transmission rate $k_x$ of the gas X is approximated from the two measurement values at times $t_0$ and $t_2$ by $$k_x = (V_{x2} - V_{x0})/(t_2 RTA) \quad (13)$$

(6) When both the transmission rates $k_x$ and $k_y$ are unknown:
In this case, the same measurement is consecutively performed upon interchanging the gases X and Y. More specifically, the second test film bag 3' (pressure P' and density $\rho_y'$) in which the gas Y is sealed is set on the electronic balance 2 mounted in the constant temperature vessel 1, and the constant temperature vessel 1 is filled with the gas X alone (pressure P' and density $\rho_x'$) and held at a measurement temperature T'. No problem arises even if the gas X is mixed into the second test film bag 3'.

Note that the mass $m_f'$ of only the bag 3' and the total area A' are measured in advance. In this case, although $m_f'$, A', and P' may differ from $m_f$, A, and P, the temperature T' in the constant temperature vessel 1 is set to be equal to the temperature T. As in the previous operation, the masses $m_0'$, $m_1'$, and $m_2'$ of the gas-filled test film bag 3' are measured at three proper times $t_0'$, $t_1'$, and $t_2'$ by the electronic balance 2.

Letting $\rho_x'$ and $\rho_y'$ be the densities of the gases X and Y at the temperature T' and pressure P', and $V_y'$ and $V_x'$ be the volumes of the gases X and Y in the second test film bag 3', volumes $V_{y0}'$, $V_{y1}'$, and $V_{y2}'$ of the gas Y in the bag at times $t_0'$, $t_1'$, and $t_2'$ are given by $$V_{y0}' = (m_0' - m_f')/(\rho_y' - \rho_x') \quad (1a')$$

$$V_{y1}' = (m_1' - m_f')/(\rho_y' - \rho_x') \quad (1b')$$

$$V_{y2}' = (m_2' - m_f')/(\rho_y' - \rho_x') \quad (1c')$$

The relationship between the volumes $V_y'$ and $V_x'$ of the gas and the transmission rates $k_y'$ and $k_x'$ is expressed by $$dV_y'/dt = -K_y'V_y'/(V_y' + V_x') \quad (2a')$$

$$dV_x'/dt = -K_x'\{V_x'/(V_y' + V_x') - 1\} \quad (2b')$$

for $$K_y' = k_y RTA' \quad (3a')$$

$$K_x' = k_x RTA' \quad (3b')$$

If equations (2a') and (2b') are solved for $V_y'$, the following result is finally obtained:

$$t = \lambda_y V_y' - C_1' \log V_y' + C_2' \quad (5')$$

for $$\lambda_y = (K_x' - K_y')/K_y'^2 \quad (6')$$

Constants $C_1'$, $C_2'$, and $\lambda_y$ are determined from three sets of measurement values at different times $t_0'$, $t_1'$, and $t_2'$. Of these constants, $\lambda_y$ is obtained by $$\lambda_y = \{a'(t_1' - t_0') - b'(t_2' - t_0')/(a'V_{y1}' - b'V_{y2}' - c'V_{y0}')\} \quad (7')$$

for $$a' = \log V_{y0}' - \log V_{y2}' \quad (8a')$$

$$b' = \log V_{y0}' - \log V_{y1}' \quad (8b')$$

$$c' = \log V_{y1}' - \log V_{y2}' \quad (8c')$$

Therefore, the transmission rates $k_x$ and $k_y$ of the two gases are obtained from the previously obtained value $\lambda_x$ and the value $\lambda_y$ obtained from the above equation.

More specifically, if $\lambda_x > 0$ and $\lambda_y < 0$, $$k_x = -1/(\lambda_x RTA) + 1/\{RT(-\lambda_x \lambda_y AA')^{1/2}\} \quad (14a)$$

$$k_y = -1/(\lambda_y RTA') - 1/\{RT(-\lambda_x \lambda_y AA')^{1/2}\} \quad (14b)$$

In addition, if $\lambda_x < 0$ and $\lambda_y > 0$, $$k_x = -1/(\lambda_x RTA) - 1/\{RT(-\lambda_x \lambda_y AA')^{1/2}\} \quad (15a)$$

$$k_y = -1/(\lambda_y RTA') + 1/\{RT(-\lambda_x \lambda_y AA')^{1/2}\} \quad (15b)$$

In actual measurement, the masses $m_0$, $m_1$, and $m_2$ at times $t_0$, $t_1$, and $t_2$ and the masses $m_0'$, $m_1'$, and $m_2'$ at times $t_0$, $t_1'$, and $t_2'$ are automatically measured, and transmission rates can be automatically output when the following equations are solved by a program in the personal computer 4 on the basis of the above measurement values and the measurement values of temperature and pressure.

An example of the program processing performed by the computer 4 will be described below.

(1) When transmission rate $k_x$ is known

Figure 4:
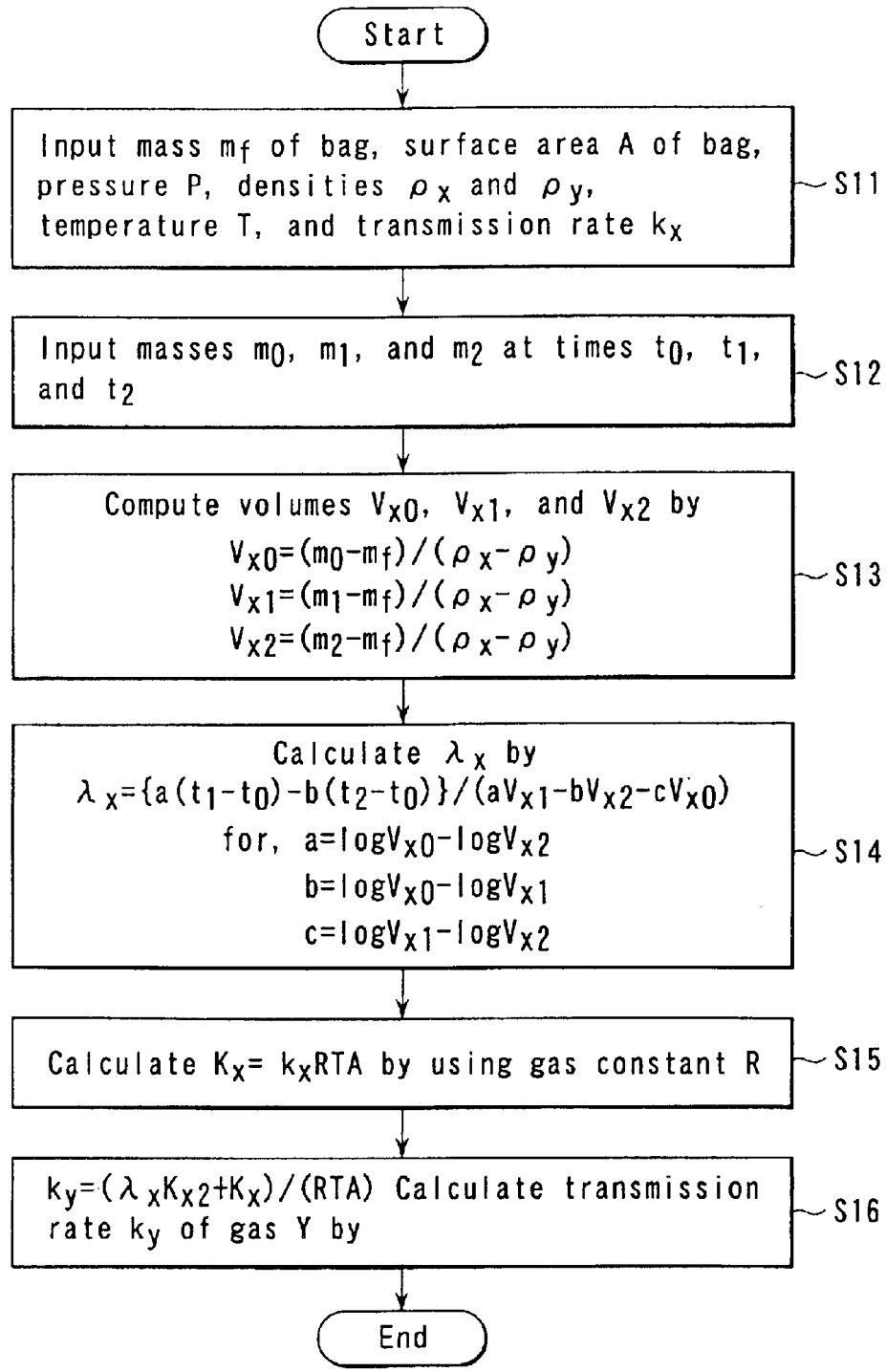
FIG. 4 is a flow chart showing a processing program for obtaining a transmission rate $k_y$ of a gas Y when a transmission rate $k_x$ of a gas X is known in the first embodiment.

FIG. 4 shows the flow of processing in this case.

Step S11: The mass $m_f$ of the test film bag 3 alone, its surface area A, the density $\rho_x$ of the gas X, density $\rho_y$ of the gas Y, the pressure P, the temperature T, and the transmission rate $k_x$ of the gas X are input.

Step S12: The measurement results on the masses $m_0$, $m_1$, and $m_2$ at times $t_0$, $t_1$, and $t_2$ are input.

Step S13: The volumes $V_{x0}$, $V_{x1}$, and $V_{x2}$ of the gas X in the test film bag 3 at times $t_0$, $t_1$, and $t_2$ are obtained by $$V_{x0}=(m_0-m_f)/(\rho_x-\rho_y)$$

$$V_{x1}=(m_1-m_f)/(\rho_x-\rho_y)$$

$$V_{x2}=(m_2-m_f)/(\rho_x-\rho_y)$$

Step S14: $\lambda_x$ is obtained by $$\lambda_x=\{a(t_1-t_0)-b(t_2-t_0)/(aV_{x1}-bV_{x2}-cV_{x0})$$

for $$a=\log V_{x0}-\log V_{x2}$$

$$b=\log V_{x0}-\log V_{x1}$$

$$c=\log V_{x1}-\log V_{x2}$$

Step S15: $K_x=k_xRTA$ (R: gas constant) is calculated by using the gas constant R.

Step S16: The transmission rate $k_y$ of the gas Y is obtained by $$k_y=(\lambda_x K_x^2+K_x)/(RTA)$$

(2) and (3) When the transmission rate $k_y$ is known

Figure 5:
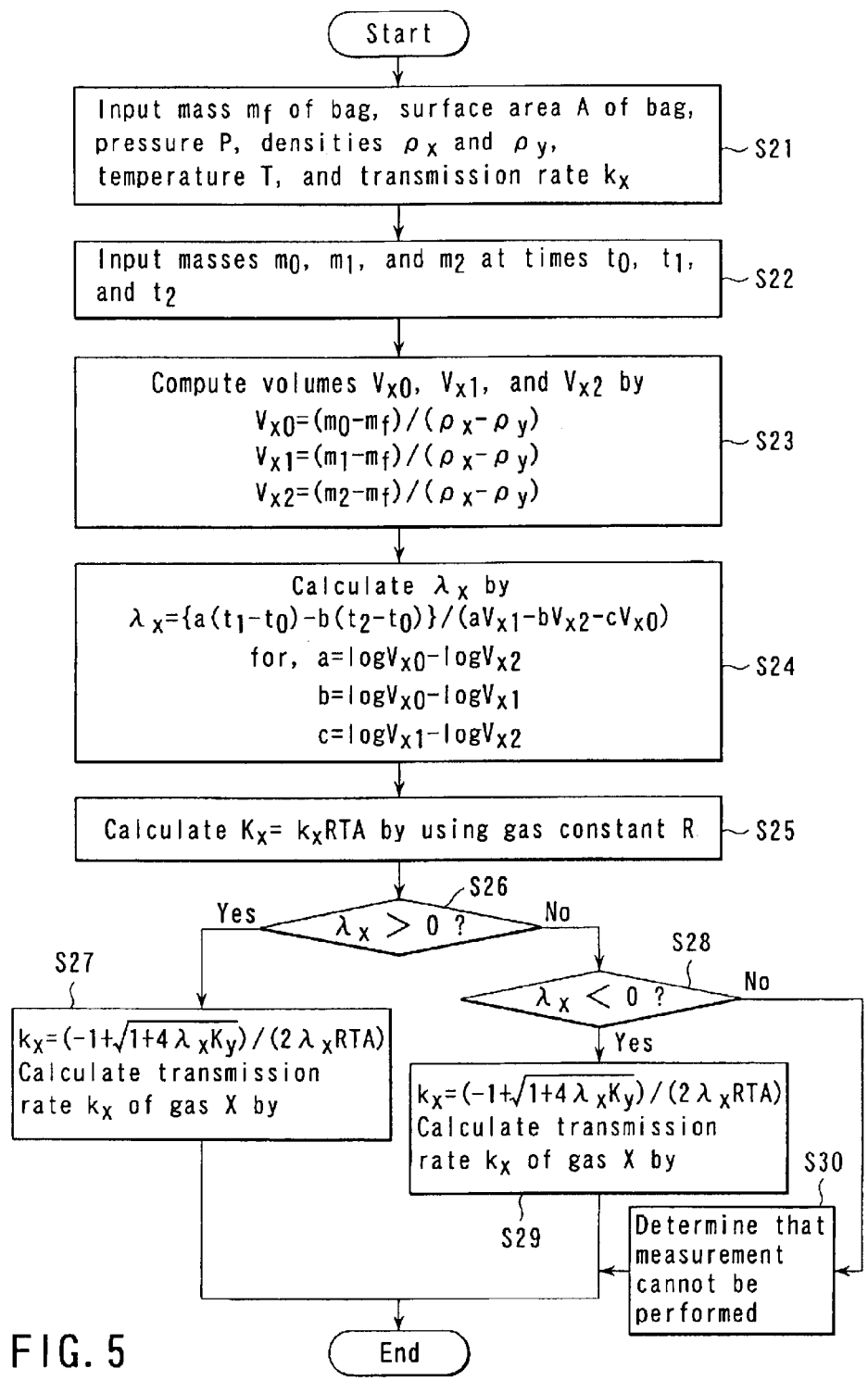
FIG. 5 is a flow chart showing a processing program for obtaining a transmission rate $k_x$ of a gas X when a transmission rate $k_y$ of a gas Y is known in the first embodiment.

FIG. 5 shows the flow of processing in this case.

Step S21: The mass $m_f$ of the test film bag 3 alone, its surface area A, the density $\rho_x$ of the gas X, density $\rho_y$ of the gas Y, the pressure P, the temperature T, and the transmission rate $k_y$ of the gas Y are input.

Step S22: The measurement results on the masses $m_0$, $m_1$, and $m_2$ at times $t_0$, $t_1$, and $t_2$ are input.

Step S23: The volumes $V_{x0}$, $V_{x1}$, and $V_{x2}$ of the gas X in the test film bag 3 at times $t_0$, $t_1$, and $t_2$ are obtained by $$V_{x0}=(m_0-m_f)/(\rho_x-\rho_y)$$

$$V_{x1}=(m_1-m_f)/(\rho_x-\rho_y)$$

$$V_{x2}=(m_2-m_f)/(\rho_x-\rho_y)$$

Step S24: $\lambda_x$ is obtained by $$\lambda_x=\{a(t_1-t_0)-b(t_2-t_0)/(aV_{x1}-bV_{x2}-cV_{x0})$$

for $$a=\log V_{x0}-\log V_{x2}$$

$$b=\log V_{x0}-\log V_{x1}$$

$$c=\log V_{x1}-\log V_{x2}$$

Step S25: $K_y=k_yRTA$ (R: gas constant) is calculated by using the gas constant R.

Step S26: It is checked whether $\lambda_x>0$.

Step S27: If $\lambda_x>0$, then the transmission rate $k_x$ of the gas X is obtained by $$k_x=\{-1+(1+4\lambda_x K_y)^{1/2}\}/(2\lambda_x RTA)$$

Step S28: If the decision in Step S26 is No, it is checked whether $\lambda_x 0$.

Step S29: If $\lambda_x<0$, then the transmission rate $k_x$ of the gas X is obtained by $$k_x=\{-1\pm(1+4\lambda_x K_y)^{1/2}\}/(2\lambda_x RTA)$$

Step S30: If $\lambda_x=0$, information indicating that the measurement cannot be done is presented.

(4) When the transmission rate $k_y$ is known and $k_x>>k_y$

Figure 6:
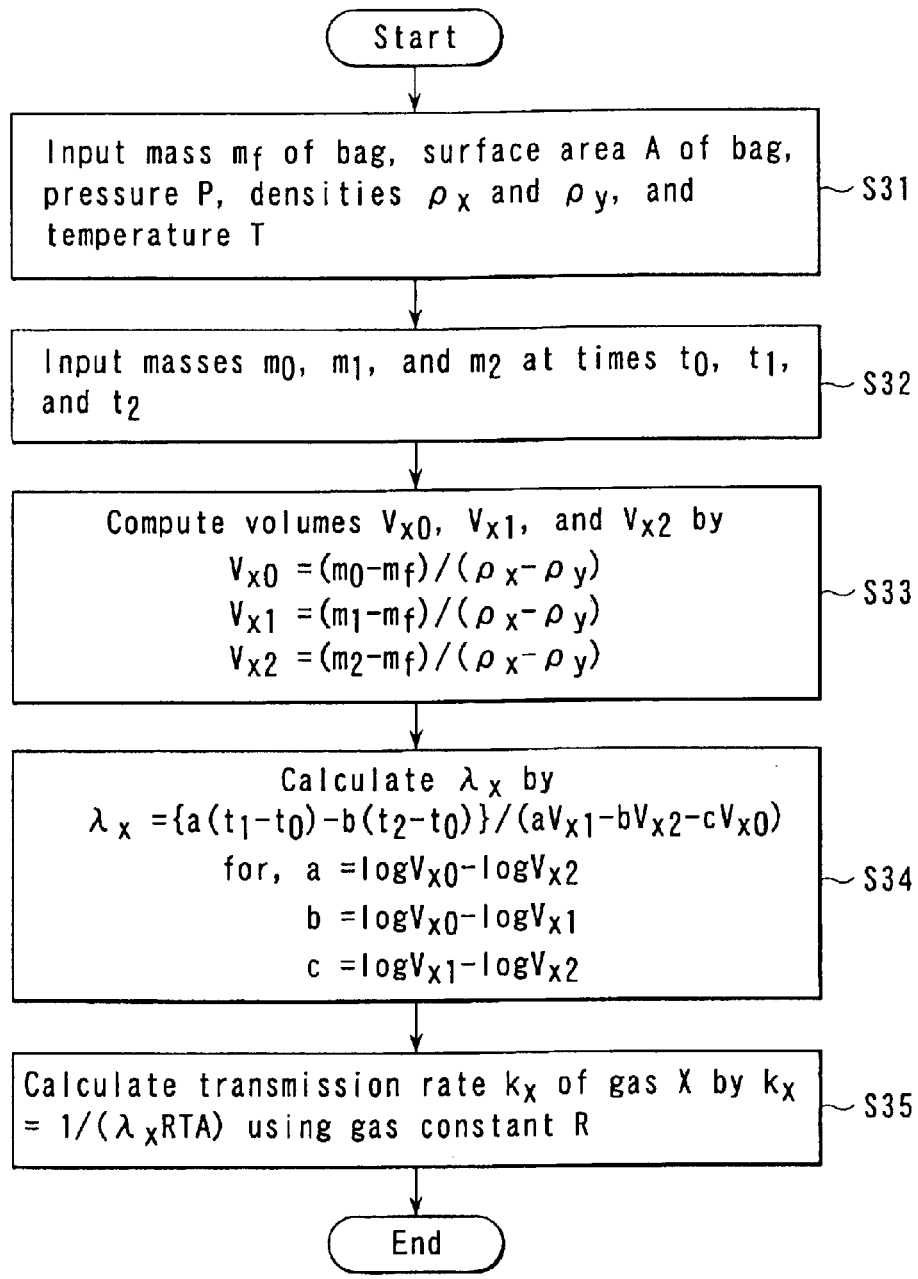
FIG. 6 is a flow chart showing a processing program for easily obtaining the transmission rate $k_x$ of the gas X when the transmission rate $k_y$ of the gas Y is known and $k_x \gg k_y$ in the first embodiment.

FIG. 6 shows the flow of processing in this case.

Step S31: The mass $m_f$ of the test film bag 3 alone, its surface area A, the density $\rho_x$ of the gas X, density $\rho_y$ of the gas Y, the pressure P, and the temperature T are input.

Step S32: The measurement results on the masses $m_0$, $m_1$, and $m_2$ at times $t_0$, $t_1$, and $t_2$ are input.

Step S33: The volumes $V_{x0}$, $V_{x1}$, and $V_{x2}$ of the gas X in the test film bag 3 at times $t_0$, $t_1$, and $t_2$ are obtained by $$V_{x0}=(m_0-m_f)/(\rho_x-\rho_y)$$

$$V_{x1}=(m_1-m_f)/(\rho_x-\rho_y)$$

$$V_{x2}=(m_2-m_f)/(\rho_x-\rho_y)$$

Step S34: $\lambda_x$ is obtained by $$\lambda_x=\{a(t_1-t_0)-b(t_2-t_0)/(aV_{x1}-bV_{x2}-cV_{x0})$$

for $$a=\log V_{x0}-\log V_{x2}$$

$$b=\log V_{x0}-\log V_{x1}$$

$$c=\log V_{x1}-\log V_{x2}$$

Step S35: The transmission rate $k_x$ of the gas X is approximated by using the gas constant R according to $$k_x=-1/(\lambda_x RTA)$$

(5) When the transmission rate $k_y$ is known, $k_x>>k_y$, and only the gas X is sealed in the bag 3

Figure 7:
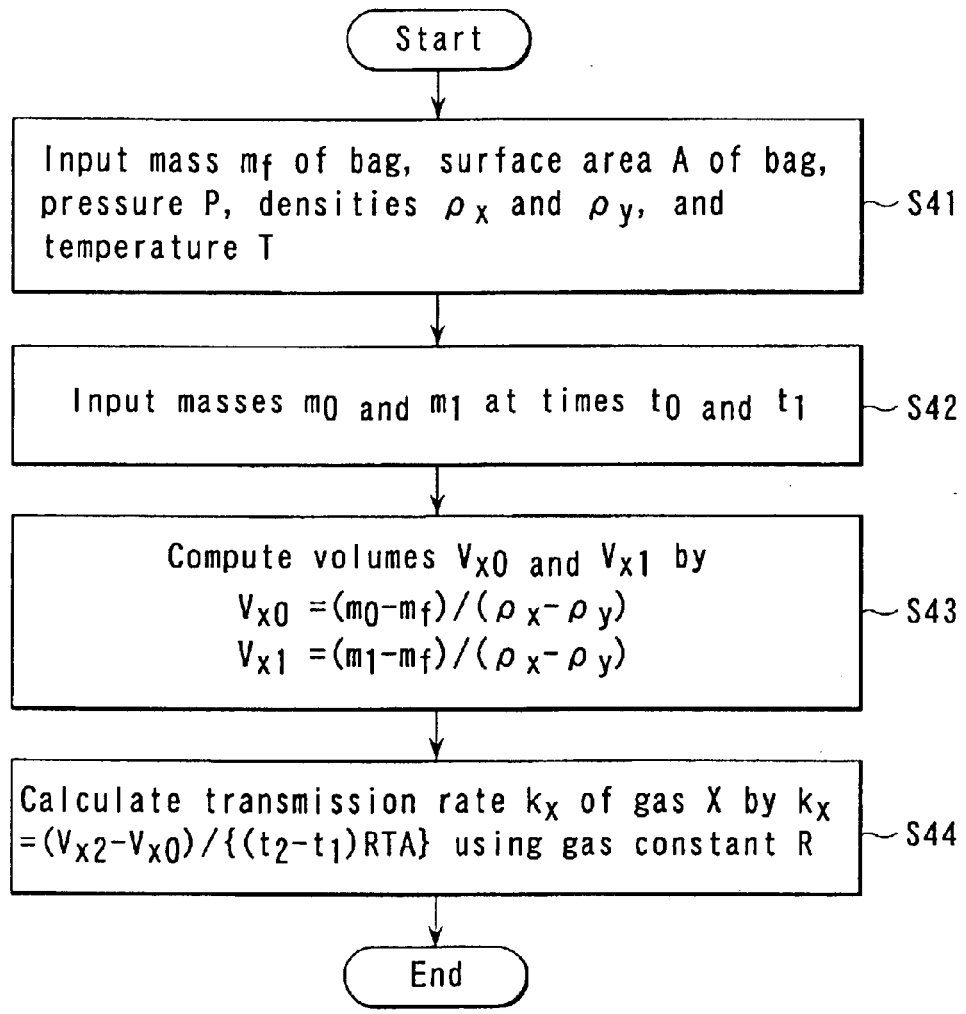
FIG. 7 is a flow chart showing a processing program for easily obtaining the transmission rate $k_x$ of the gas X when the transmission rate $k_y$ is known and $k_x \gg k_y$ in the first embodiment.

FIG. 7 shows the flow of processing in this case.

Step S41: The mass $m_f$ of the test film bag 3 alone, its surface area A, the density $\rho_x$ of the gas X, density $\rho_y$ of the gas Y, the pressure P, and the temperature T are input.

Step S42: The measurement results on the masses $m_0$ and $m_1$ at times $t_0$ and $t_1$ are input.

Step S43: The volumes $V_{x0}$ and $V_{x1}$ of the gas X in the test film bag 3 at times $t_o$ and $t_1$ are obtained by $$V_{x0}=(m_0-m_f)/(\rho_x-\rho_y)$$

$$V_{x1}=(m_1-m_f)/(\rho_x-\rho_y)$$

Step S44: The transmission rate $k_x$ of the gas X is approximated by using the gas constant R according to $$k_x=(V_{x1}-V_{x0})/\{(t_1-t_0)RTA\}$$

Since two measurement values suffice under a certain condition, state 1 is skipped.

(6) When both the transmission rates $k_x$ and $k_y$ are unknown

Figure 8A:
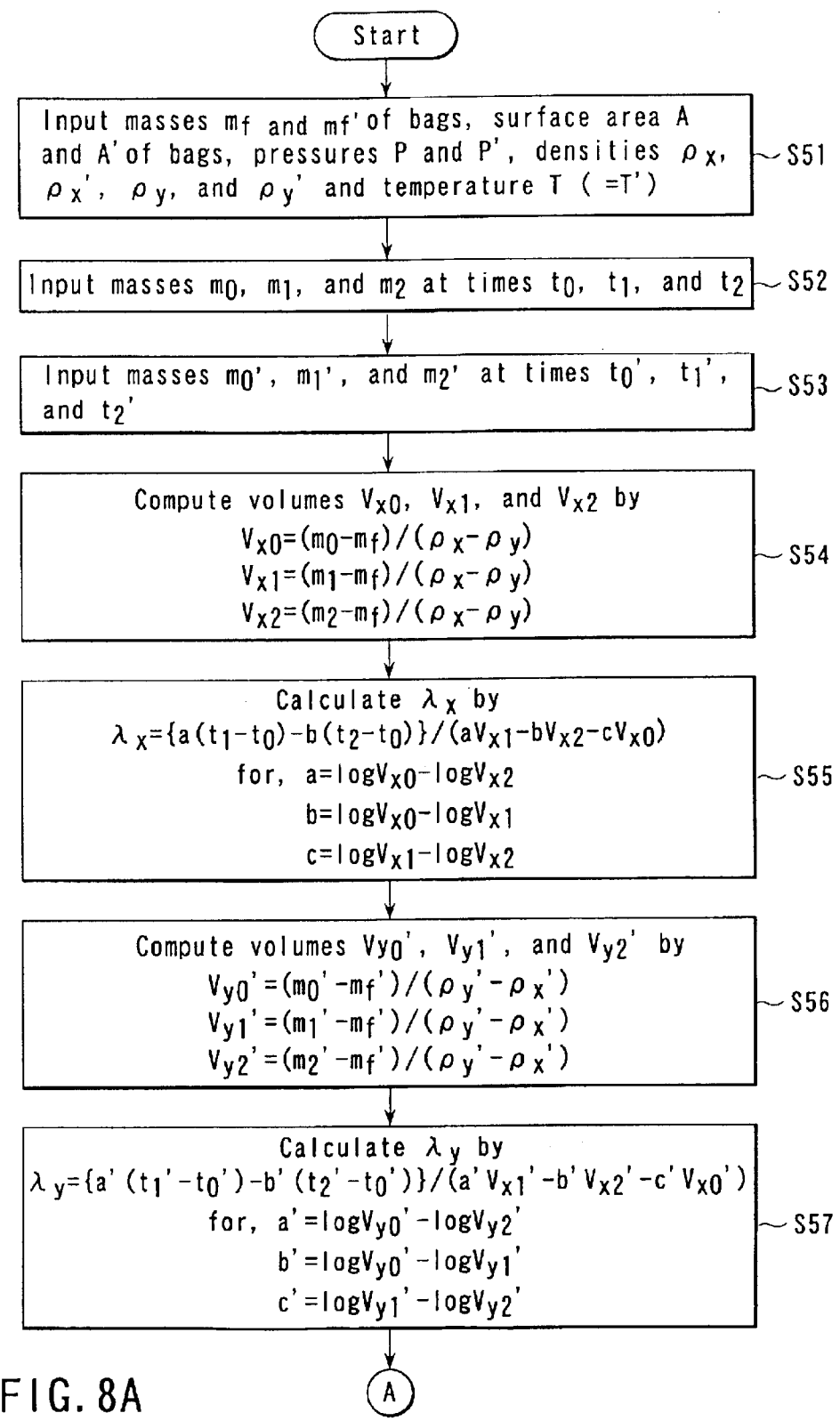
FIGS. 8A and 8B are a flow chart showing a processing program for obtaining both the transmission rate $k_x$ of the gas X and the transmission rate $k_y$ of the gas Y when the two transmission rates are unknown in the first embodiment.
Figure 8B:
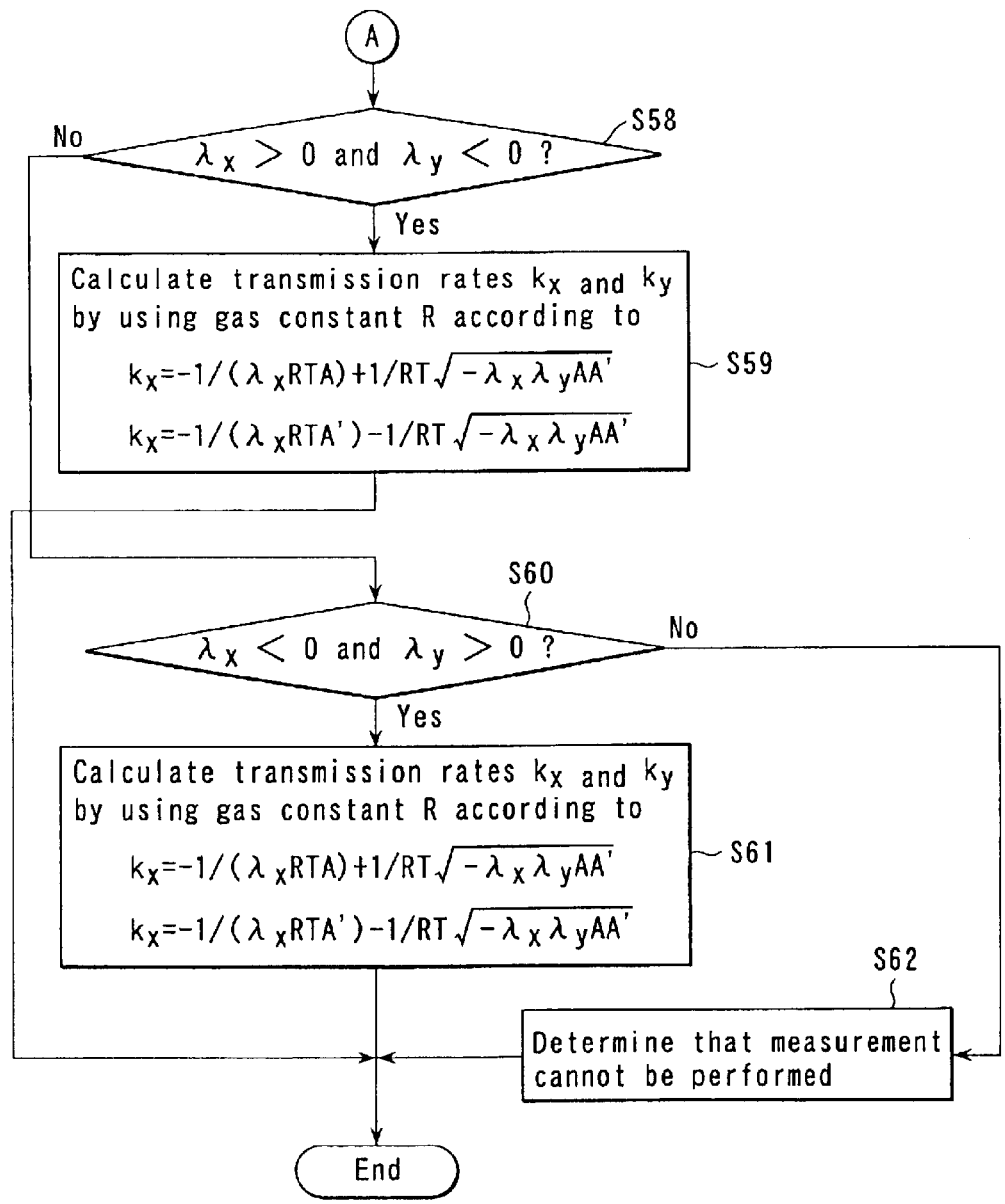

FIGS. 8A and 8B show the flow of processing in this case.

Step S51: The masses $m_f$ and $m_f'$ of the first and second test film bags 3 and 31 alone and their surface areas A and A' are input, together with the values obtained when the gas X is sealed in the bag 3, i.e., the density $\rho_x$ of the gas X, density $\rho_y$ of the gas Y, the pressure P, and the temperature T, and the values obtained when the gas Y is sealed in the bag 3', i.e., the density $\rho_x'$ of the gas X, density $\rho_y'$ of the gas Y, the pressure P', and the temperature T' (=T).

Step S52: The measurement results on the masses $m_0$, $m_1$, and $m_2$ at times $t_0$, $t_1$, and $t_2$ when the gas X is sealed in the first test film bag 3 are input.

Step S53: The measurement results on the masses $m_0'$, $m_1'$, and $m_2'$ at times $t_0'$, $t_1'$, and $t_2'$ when the gas Y is sealed in the second test film bag 3' are input.

Step S54: The volumes $V_{x0}$, $V_{x1}$, and $V_{x2}$ of the gas X in the first test film bag 3 at times $t_0$, $t_1$, and $t_2$ when the gas X is sealed in the first test film bag 3 are obtained by $$V_{x0}=(m_0-m_f)/(\rho_x-\rho_y)$$

$$V_{x1}=(m_1-m_f)/(\rho_x-\rho_y)$$

$$V_{x2}=(m_2-m_f)/(\rho_x-\rho_y)$$

Step S55: $\lambda_x$ is obtained by $$\lambda_x=\{a(t_1-t_0)-b(t_2-t_0)/(aV_{x1}-bV_{x2}-cV_{x0})$$

for $$a=\log V_{x0}-\log V_{x2}$$

$$b=\log V_{x0}-\log V_{x1}$$

$$c=\log V_{x1}-\log V_{x2}$$

Step S56: The volumes $V_{y0}'$, $V_{y1}'$, and $V_{y2}'$ of the gas Y in the second test film bag 3' at times $t_0'$, $t_1'$, and $t_2'$ when the gas Y is sealed in the second test film bag 3' are obtained by $$V_{y0}=(m_0-m_f)/(\rho_y-\rho_x)$$

$$V_{y1}=(m_1-m_f)/(\rho_y-\rho_x)$$

$$V_{y2}=(m_2-m_f)/(\rho_y-\rho_x)$$

Step S57: $\lambda_x$ is obtained by $$\lambda_y=\{a'(t_1'-t_0')-b'(t_2'-t_0')\}/(a'V_{y1}'-b''V_{y2}'-c'V_{y0}')$$

for $$a'=\log V_{y0}'-\log V_{y2}'$$

$$b'=\log V_{y0}'-\log V_{y1}'$$

$$c'=\log V_{y1}'-\log V_{y2}'$$

Step S58: It is checked whether $\lambda_x>0$ and $\lambda_y<0$.

Step S59: If $\lambda_x>0$ and $\lambda_y<0$, the transmission rate $k_x$ of the gas X and the transmission rate $k_y$ of the gas Y are obtained by using the gas constant R according to $$k_x=-1/(\lambda_x RTA)+1/\{RT(-\lambda_x\lambda_y AA')^{1/2}\}$$

$$k_y=-1/(\lambda_y RTA')-1/\{RT(-\lambda_x\lambda_y AA')^{1/2}\}$$

Step S60: If $\lambda_x<0$ or $\lambda_y>0$, it is checked whether $\lambda_x<0$ and $\lambda_y>0$.

Step S61: If $\lambda_x<0$ and $\lambda_y>0$, the transmission rate $k_x$ of the gas X and the transmission rate $k_y$ of the gas Y are obtained by using the gas constant R according to $$k_x=-1/(\lambda_x RTA)-1/\{RT(-\lambda_x\lambda_y AA')^{1/2}\}$$

$$k_y=-1/(\lambda_y RTA')+1/\{RT(-\lambda_x\lambda_y AA')^{1/2}\}$$

Step S62: If the decision made at step S60 is No, it is determined that the measurement cannot be done, and the processing is terminated.

The transmission rate of a plastic film can be easily and accurately measured by making the computer 4 execute the above program.

The above embodiment has exemplified the method of obtaining gas transmission rates from measurement values at two or three points. However, gas transmission rates can be accurately calculated from more measurement points. In addition, the measurement time and measurement precision can be properly adjusted in accordance with the precision of the electronic balance 2 by changing the size of the test film bag 3.

In the above embodiment, as described in (6), when both the transmission rates $k_x$ and $k_y$ are unknown, the second measurement is performed upon interchanging the gases X and Y. Instead of this method, however, a method of calculating transmission rates according equation (4) by calculating the volume $V_{y2}$ by replacing the gas Y in the constant temperature vessel 1 with the gas X immediately after the first measurement of $V_{y2}$. In this case, the volume $V_{y0}$ of the gas Y in the bag at time $t_0$ needs to be equal to 0.

The following is a measurement example.

Nitrogen and oxygen were used as the gases X and Y, respectively, and the following measurement values were obtained at a temperature of 25 [° C.] and a pressure of 1009 [hpa]. Note that gas constant R=8.3145 [J/molK].

$m_f$=2020.00 [mg], A=0.0445 [m$^2$]

at first (t=0[s]):$m_0$=1965.20 [mg]

after 9,200 sec ($t_1$=9200[s]):$m_1$=1966.74 [mg]

after 10,800 sec ($t_2$=20000[s]):$m_2$=1968.19 [mg]

A measurement was performed at the same temperature upon interchanging the gases X and Y to obtain the following measurement values. The pressure was 1,017 [hPa].

$m_f'$=2088.00 [mg], A'=0.0452 [m$^2$]

at first (t=0[s]): $m_0'$=2149.15 [mg]

after 1,490 sec ($t_1'$=1490[s]):$m_1'$=2147.49 [mg]

after 1,510 sec ($t_2'$=30000[s]):$m_2'$=2145.78 [mg]

Assume that the density difference between the gas X and the gas Y in the respective test temperature/pressure environments are $$\rho_x-\rho_y=-0.162357 \text{ [kg/m}^3\text{]}$$

$$\rho_y'-\rho_x'=0.163645 \text{ [kg/m}^3\text{]}$$

Substitutions of the measurement values into equations (1a) to (1c) and (1a') to (1c') for obtaining the respective volumes yield:

$V_{x0}$=0.000337527 [m$^3$]

$V_{x1}$=0.000328042 [m$^3$]

$V_{x2}$=0.000319111 [m$^3$]

$V_{y0}'$=0.000373676 [m$^3$]

$V_{y1}'$=0.000363532 [m$^3$]

$V_{y2}'$=0.000353082 [m$^3$]

In addition, substitutions of the above results into equations (7) and (7') for obtaining $\lambda_x$ and $\lambda_y$ yield:

$$\lambda_x=7.44241\times10^9$$

$$\lambda_y=-2.29725\times10^8$$

Since $\lambda_x>0$ and $\lambda_y<0$, the respective transmission rates $k_x$ and $k_y$ are determined from equations (14a) and (14b) as follows:

$$k_x=5.66\times10^{-12} \text{ [mol/m}^2\text{sPa]}$$

$$k_y=3.20\times10^{-11} \text{ [mol/m}^2\text{sPa]}$$

As is obvious from the above measurement example, according to this embodiment, the transmission rates $k_x$ and $k_y$ of the dry gases X and Y through a test film can be accurately measured by a simple measuring apparatus. (When the saturation vapor pressure is lower than atmospheric pressure)

In this case, two methods are available. One method is a method of reducing the pressure in the constant temperature vessel 1 to make the saturation vapor pressure become higher than the pressure in the constant temperature vessel 1. In this case, the measurement method is the same as that for dry gases, and hence a description thereof will be omitted. A method of measuring gas transmission rates under atmospheric pressure will be described below.

Figure 9:
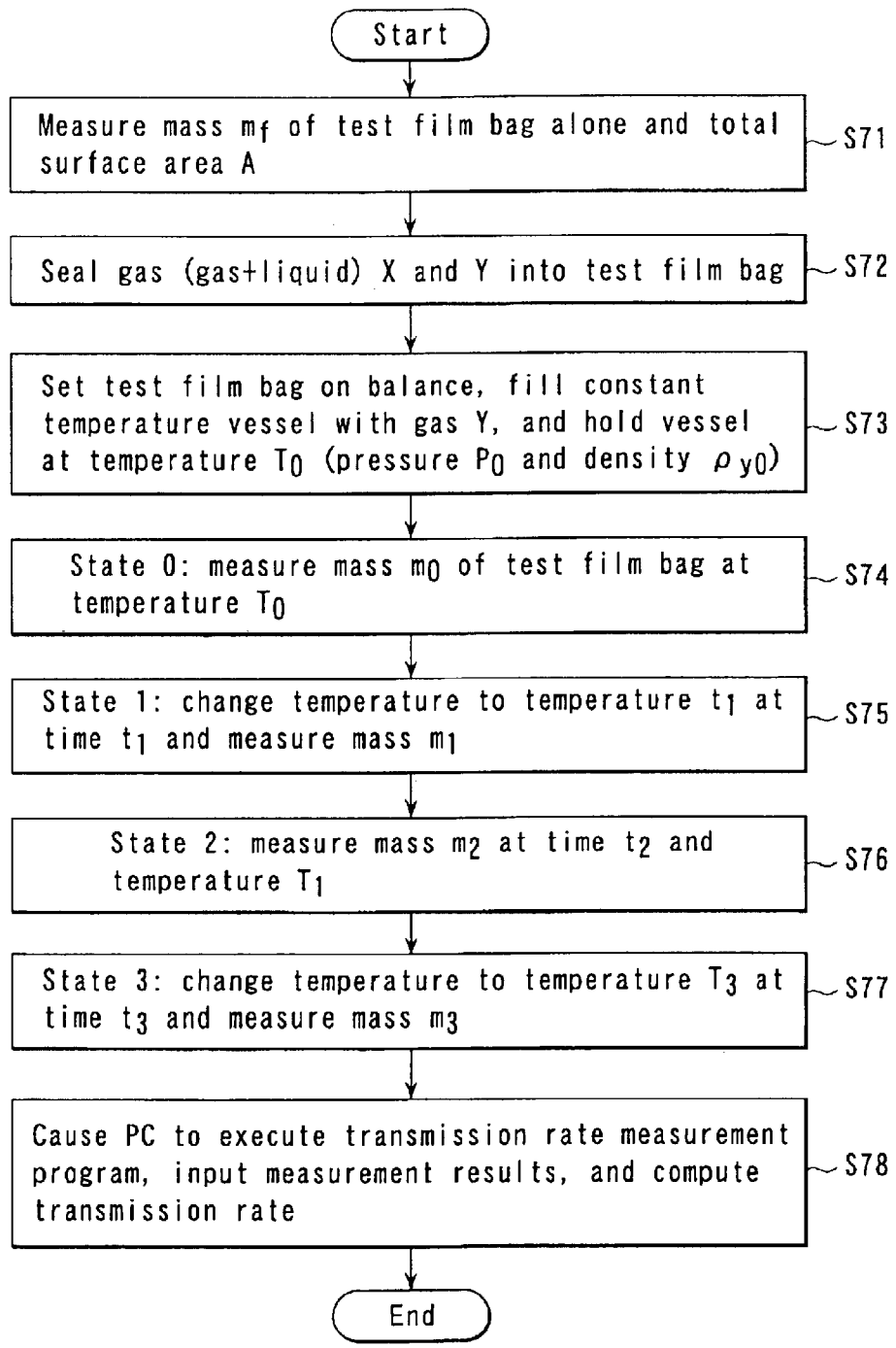
FIG. 9 is a flow chart showing the flow of measurement processing when a gas whose saturation vapor pressure is lower than atmospheric pressure is used as a gas to be measured in the second embodiment of the present invention.

A case wherein the transmission rate $k_x$ [kg/m²sPa] of the gas X whose vapor pressure at room temperature is lower than atmospheric pressure is measured with respect to a plastic film having a given thickness will be described in accordance with the procedure shown in FIG. 9. Assume that in this case, for example, water vapor and nitrogen are used as gases X and Y, respectively.

First of all, as in the case of dry gases, a specimen (to be referred to as the test film bag hereinafter) 3 formed by processing a test film into a bag is prepared, and a mass $m_f$ [kg] of the bag alone and a total area A [m²] associated with the transmission of a gas are measured in advance (step S71). Water vapor and nitrogen are sealed, as the gases X and Y, into the test film bag 3 in proper amounts (step S72). At this time, water liquid is always left in the bag 3. That is, the water vapor in the bag 3 is always kept saturated.

In this case, no problem arises even if the gas Y is mixed in the gas X. The amount of the water vapor X sealed is set to an amount at which no pressure acts on the bag 3 during the test under a test environmental temperature/pressure condition. That is, the internal pressure of the bag 3 is always kept equal to the pressure in a constant temperature vessel 1.

Note, however, that the water vapor should be sealed in the test film bag 3 in amount sufficient to prevent portions of the inner surface of the test film bag 3 from coming into contact with each other. Alternatively, an unwoven fabric or structure that has no influence on this measurement may be inserted in the bag 3 to form a gap. In this case, care should be taken not to change the area of the surface through which the gas is transmitted and set a negative pressure in the bag 3 upon transmission of the water vapor X.

Figure 10A:
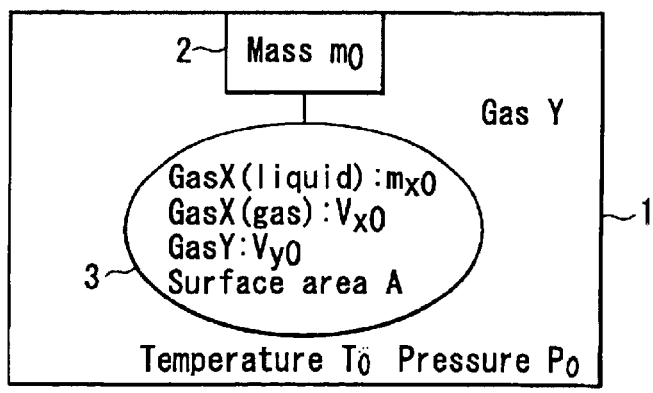
FIGS. 10A to 10D are conceptual views respectively showing set environments for states 0 to 3 along the procedure in the second embodiment.

Subsequently, as shown in FIG. 10A, the test film bag 3 is suspended from an electronic balance 2 mounted in the constant temperature vessel 1, and the constant temperature vessel 1 is filled with the gas Y alone and held at a temperature $T_0$ [K] (pressure $P_0$ [Pa] and density $\rho_y$) (step S73). At this time, the volume of the constant temperature vessel 1 is sufficiently larger than the volume of the bag 3, and the pressure in the constant temperature vessel 1 is always equal to atmospheric pressure.

Figure 10B:
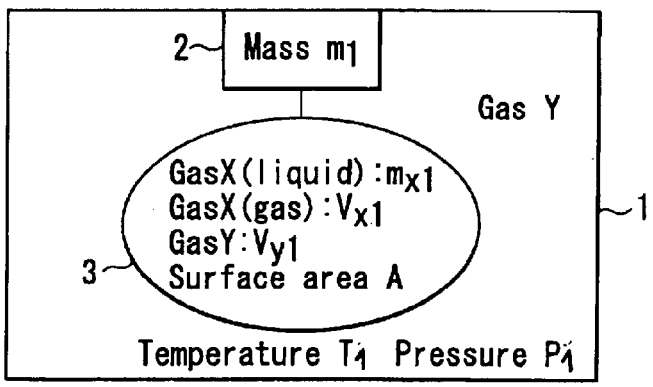
Figure 10C:
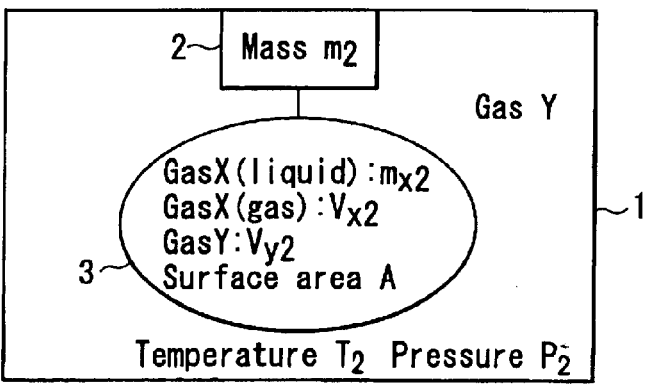
Figure 10D:
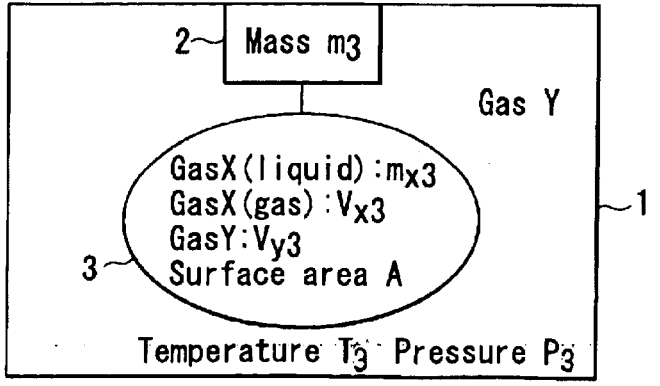

A value (mass) $m_0$ [kg] obtained by dividing the measured weight by the gravitational acceleration at a measurement place is measured by the electronic balance 2 in the constant temperature vessel 1 (temperature $T_0$ [K] and pressure $P_0$ [Pa]) filled with the gas Y alone (step S74). Assume that the state at this time is represented by state 0. In addition, as shown in FIG. 10B, the internal temperature in the constant temperature vessel 1 is changed to a test temperature $T_1$ [K] (pressure $P_1$ [Pa]), and a measurement value $m_1$ [kg] is obtained in the same manner as described above (step S75). The state at this time is represented by state 1, and the time is represented by $t_1$. Thereafter, as shown in FIG. 10C, a measurement value $m_2$ is obtained at time $t_2$ (step S76). The state at this time is represented by state 2. Furthermore, as shown in FIG. 10D, the internal temperature of the constant temperature vessel 1 is changed to $T_3$ [K] (pressure $P_3$ [Pa]), and a measurement value $m_3$ [kg] is obtained (step S77). The state at this time is represented by state 3.

Since the time required to change state 0 to state 1 and from state 2 to state 3 is sufficiently shorter than the measurement time $t_2-t_1$, and hence the gas transmission amount in this interval can be neglected.

After the above measurement, the computer 4 is caused to execute the transmission rate measurement program, and measurement results are input, thereby making a computer 4 calculate transmission rates (step S78).

Note that when the computer 4 executes the program, temperature control on the constant temperature vessel 1 and acquisition of measured masses may be automatically performed.

The transmission rate computation processing in this measurement will be described below.

First of all, the mass of water, the volume of the gas (water vapor) X, and the volume of the gas Y have the following relationship according to the Archimedean principle:

$$m_0 - m_f = m_{x0} + (\rho_{x0} - \rho_{y0})V_{x0} \tag{16a}$$

$$m_1 - m_f = m_{x1} + (\rho_x - \rho_y)V_{x1} \tag{16b}$$

$$m_2 - m_f = m_{x2} + (\rho_x - \rho_y)V_{x2} \tag{16c}$$

$$m_3 - m_f = m_{x3} + (\rho_{x3} - \rho_{y3})V_{x3} \tag{16d}$$

Since changes from state 0 to state 1 and from state 2 to state 3 are made within short periods of time, it is assumed that no gas transmission occurs. Since the total amount of water and the amount of the gas Y remain the same between these states, $$\rho_{y0} V_{y0} = \rho_y V_{y1} \tag{17a}$$

$$m_{x0} + \rho_{x0} V_{x0} = m_{x1} + \rho_x V_{x1} \tag{17b}$$

$$\rho_y V_{y2} = \rho_{y3} V_{y3} \tag{17c}$$

$$m_{x2} + \rho_x V_{x2} = m_{x3} + \rho_{x3} V_{x3} \tag{17d}$$

In addition, since the gas (water vapor) X is always kept saturated, $$V_{x0}/(V_{x0}+V_{y0}) = P_{x0}/P_0 \tag{18a}$$

$$V_{x1}/(V_{x1}+V_{y1}) = P_x/P \tag{18b}$$

$$V_{x2}/(V_{x2}+V_{y2}) = P_x/P \tag{18c}$$

$$V_{x3}/(V_{x3}+V_{y3}) = P_{x3}/P_3 \tag{18d}$$

where $P_{x0}$, $P_x$, and $P_{x3}$ are the saturation vapor pressures of the gas (water vapor) X at temperatures $T_0$, $T_1$, and $T_3$.

The total mass of the water (liquid and gas) of the gas X in states 1 and 2 is obtained as follows from equations (16a) to (18d). This total mass can be calculated from four sets of measurement values.

$$m_{x1}+\rho_{x1}V_{x1}=m_1-m_f+(m_0-m_1)(P_0/P_{x0}-1)/(P_0/P_{x0}-P_1/P_{x1}) \tag{19a}$$

$$m_{x2}+\rho_{x2}V_{x2}=m_3-m_f+(m_2-m_3)(P_1/P_{x2}-1)/(P_1/P_{x2}-P_3/P_{x3}) \tag{19b}$$

Therefore, the transmission rate of the gas (water vapor) X can be obtained by $$k_x = \{(m_{x1}+\rho_{x1}V_{x1})-(m_{x2}+\rho_{x2}V_{x2})\}/(t_2 P_x A) \tag{20}$$

Figure 11:
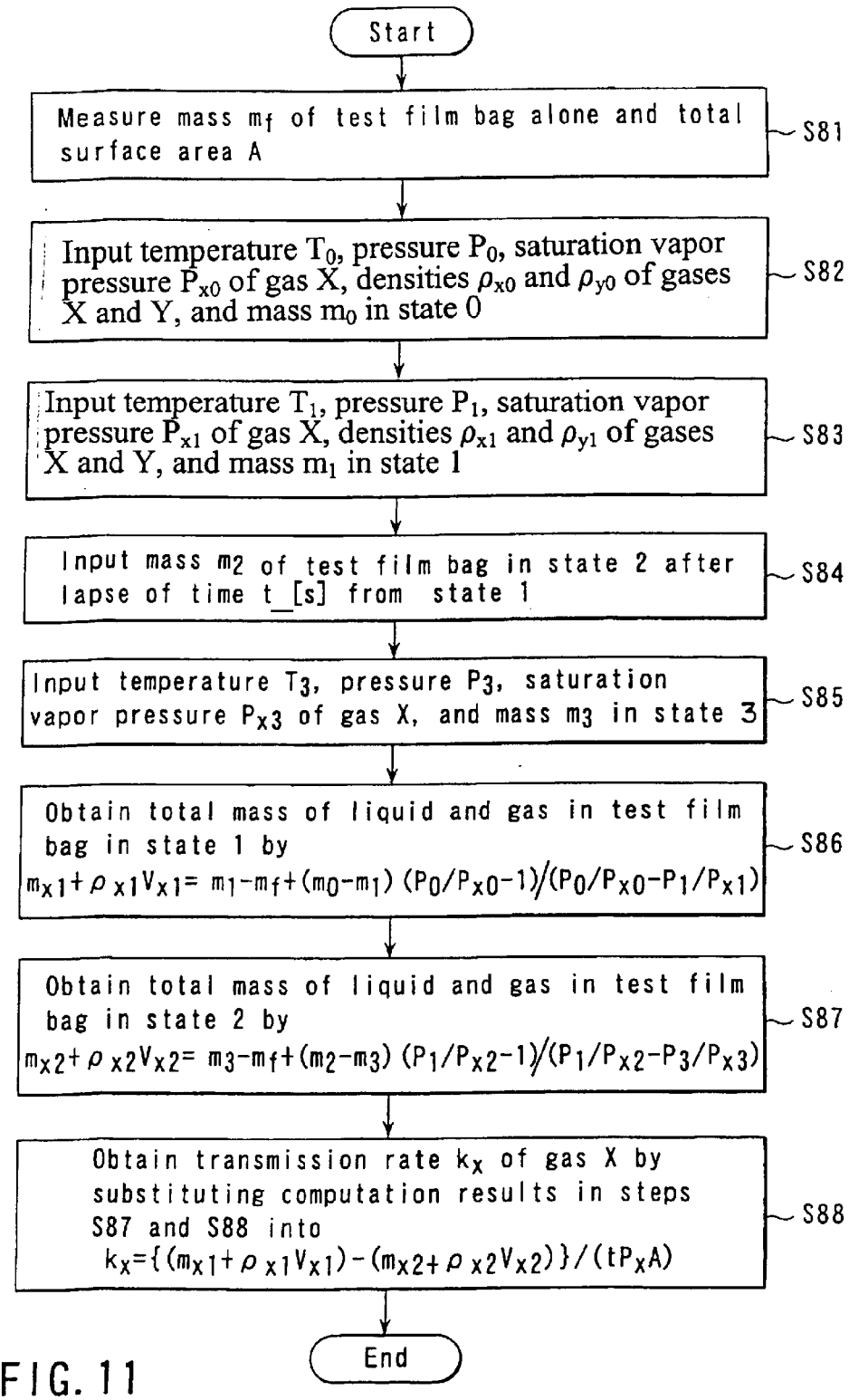
FIG. 11 is a flow chart showing a processing program for obtaining the transmission rate of a gas whose saturation vapor pressure is lower than atmospheric pressure in the second embodiment.

An example of the program processing executed by the computer 4 in this case will be described below with respect to FIG. 11.

Step S81: The mass $m_f$ of the test film bag 3 alone and its total surface area A are input.

Step S82: The respective values in state 0, i.e., the internal temperature $T_0$, the pressure $P_0$, the saturation vapor pressure $P_{x0}$ of the gas X, the density $\rho_{x0}$ of the gas X, and the density $\rho_{y0}$ of the gas Y are input, together with the mass measurement result $m_0$ of the test film bag 3.

Step S83: The respective values in state 1, i.e., the internal temperature $T_1$, the pressure $P_1$, the saturation vapor pressure $P_{x1}$ of the gas X, the density $\rho_{x1}$ of the gas X, and the density $\rho_{y1}$ of the gas Y are input, together with the mass measurement result $m_1$ of the test film bag 3.

Step S84: The measurement result on the mass $m_2$ of the gas-filled test film bag 3 in state 2 after a lapse of t [s] from state 1 is input.

Step S85: The respective values in state 3, i.e., the internal temperature $T_3$, the pressure $P_3$, and the saturation vapor pressure $P_{x3}$ of the gas X are input, together with the mass measurement result $m_3$ of the test film bag 3.

Step S86: The total mass of the liquid and gas in the test film bag 3 in state 1 is obtained by $$m_{x1}+\rho_{x1}V_{x1}=m_1-m_f+(m_0-m_1)(P_0/P_{x0}-1)/(P_0/P_{x0}-P_1/P_{x1})$$

Step S87: The total mass of the liquid and gas in the test film bag 3 in state 2 is obtained by $$m_{x2}+\rho_{x2}V_{x2}=m_3-m_f+(m_2-m_3)(P_1/P_{x2}-1)/(P_1/P_{x2}-P_3/P_{x3})$$

Step S88: The transmission rate $k_x$ is obtained by substituting the computation results in steps S87 and S88 into $$k_x=\{(m_{x1}+\rho_{x1}V_{x1})-(m_{x2}+\rho_{x2}V_{x2})\}/(tP_xA)$$

The following is a measurement example.

Water vapor and nitrogen were used as the gases X and Y, respectively, and the following measurement values were obtained. Note that the pressure was fixed to 1,013 [hPa] and gas constant R=8.3145 [J/molK].

$m_f$=2050.00 [mg], A=0.0502 [m$^2$]
state 0: temperature of 20° C. and $m_0$=2456.52 [mg]
state 1: temperature of 40° C. and $m_1$=2454.39 [mg]
state 2 (after 1,000 sec, i.e., $t_2$=1000 [s]): temperature of 40° C. and $m_2$=2431.61 [mg]
state 3: temperature of 20° C. and $m_3$=2433.78 [mg]

In addition, assume that the vapor pressures at the respective temperatures are $P_{x0}$=2313 [Pa]

$P_x$=7359 [Pa]

$P_{x3}$=2313 [Pa]

Substitutions of the measurement values into equations (19a) and (19b) for obtaining the total mass of water yield $m_{x1}+\rho_{x1}V_{x1}$=407.43 [Pa]

$m_{x2}+\rho_{x2}V_{x2}$=384.70 [Pa]

Therefore, the transmission rate of the water vapor X is determined as follows from equation (20):
$k_x$=6.15×10$^{-11}$ [kg/m$^2$sPa]

As is obvious from the above measurement example, according to this embodiment, the transmission rate $k_x$ of the gas X, whose saturation vapor pressure is lower than atmospheric pressure, through a test film can be accurately measured by a simple measuring apparatus.

Various modifications and changes can be made without departing from the spirit and scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of measuring a gas transmission rate of a plastic film, comprising:

sealing a gas X into a test film bag which is formed by processing a test plastic film into a bag and has known mass and surface area;

measuring a mass of the test film bag in which the gas is sealed, a plurality of numbers of times on the time series, while keeping a temperature constant in a temperature-controlled airtight vessel which is filled with a gas Y different from the gas X so as to make a pressure in the vessel equal to an internal pressure of the test film bag; and obtaining a transmission rate (a value representing the number of moles of a gas transmitted through a test piece with a unit area in a unit time at a unit partial pressure difference) associated with the gas X from a relationship between the measurement results, the mass of the test film bag alone, and the surface area.

2. A method of measuring a gas transmission rate of a plastic film, in which when a transmission rate (a value representing the number of moles of a gas transmitted through a test piece with a unit area in a unit time at a unit partial pressure difference) $k_x$ [mol/m$^2$sPa] of a gas X is known, a transmission rate $k_y$ [mol/m$^2$sPa] of a gas Y through a test plastic film is measured, comprising:

preparing a test film bag by processing the test plastic film into a bag, and measuring a mass $m_f$ [kg] of the test film bag alone and a total surface area A [m$^2$] associated with gas transmission in advance;

sealing the gas X into the test film bag at a density $\rho_x$, and measuring masses $m_0$ [kg], $m_1$ [kg], and $m_2$ [kg] of the test film bag in which the gas is sealed at least at times $t_0$ [s], $t_1$ [s], and $t_2$ [s] in an airtight vessel which is filled with the gas Y at a density $\rho_y$ so as to set a pressure P [Pa] equal to an internal pressure of the test film bag and in which a temperature is kept constant at a measurement temperature T [K];

obtaining volumes $V_{x0}$, $V_{x1}$, and $V_{x2}$ of the gas X in the test film bag at times $t_0$, $t_1$, and $t_2$ from $V_{x0}=(m_0-m_f)/(\rho_x-\rho_y)$ $V_{x1}=(m_1-m_f)/(\rho_x-\rho_y)$ $V_{x2}=(m_2-m_f)/(\rho_x-\rho_y)$ obtaining $\lambda_x$ by substituting the obtained results into the following equation for obtaining $\lambda_x$:

$\lambda_x=\{a(t_1-t_0)-b(t_2-t_0)\}/(aV_{x1}-bV_{x2}-cV_{x0}$ for $b$=log $V_{x0}$−log $V_{x1}$ $c$=log $V_{x1}$−log $V_{x2}$ and
computing $$k_y=(\lambda_x K_x^2+K_x)/(RTA)$$

where R is a gas constant and $K_x=k_x RTA$ thereby obtaining the transmission rate $k_y$ of the gas Y when the transmission rate $k_x$ is known.

3. A method of measuring a gas transmission rate of a plastic film, in which when a transmission rate (a value representing the number of moles of a gas transmitted through a test piece with a unit area in a unit time at a unit partial pressure difference) $k_y$ [mol/m²sPa] of a gas Y is known, a transmission rate $k_x$ [mol/m²sPa] of a gas X through a test plastic film is measured, comprising:

preparing a test film bag by processing the test plastic film into a bag, and measuring a mass $m_f$ [kg] of the test film bag alone and a total surface area A [m²] associated with gas transmission in advance;

sealing the gas X into the test film bag at a density $\rho_x$, and measuring masses $m_0$ [kg], $m_1$ [kg], and $m_2$ [kg] of the test film bag in which the gas is sealed at least at times $t_0$ [s], $t_1$ [s], and $t_2$ [s] in an airtight vessel which is filled with the gas Y at a density $\rho_y$ so as to set a pressure P [Pa] equal to an internal pressure of the test film bag and in which a temperature is kept constant at a measurement temperature T [K];

obtaining volumes $V_{x0}$, $V_{x1}$, and $V_{x2}$ of the gas X in the test film bag at times $t_0$, $t_1$, and $t_2$ from $$V_{x0}=(m_0-m_f)/(\rho_x-\rho_y)$$

$$V_{x1}=(m_1-m_f)/(\rho_x-\rho_y)$$

$$V_{x2}=(m_2-m_f)/(\rho_x-\rho_y)$$

obtaining $\lambda_x$ by substituting the obtained results into the following equation for obtaining $\lambda_x$:

$$\lambda_x=\{a(t_1-t_0)-b(t_2-t_0)\}/(aV_{x1}-bV_{x2}-cV_{x0})$$

for $$a=\log V_{x0}-\log V_{x2}$$

$$b=\log V_{x0}-\log V_{x1}$$

$$c=\log V_{x1}-\log V_{x2}$$

and
when $\lambda_x>0$, computing $$k_x=\{-1+(1+4\lambda_x K_y)^{1/2}\}/(2\lambda_x RTA)$$

where R is a gas constant and $K_x=k_x RTA$ and when $\lambda_x<0$, computing $$k_x=\{-1\pm(1+4\lambda_x K_y)^{1/2}\}/(2\lambda_x RTA)$$

thereby obtaining the transmission rate $k_x$ of the gas X when the transmission rate $k_y$ is known.

4. A method of measuring a gas transmission rate of a plastic film, in which when a transmission rate (a value representing the number of moles of a gas transmitted through a test piece with a unit area in a unit time at a unit partial pressure difference) $k_y$ [mol/m²sPa] of a gas Y is known, a transmission rate $k_x$ [mol/m²sPa] of a gas X through a test plastic film ($k_x \gg k_y$) is measured, comprising:

preparing a test film bag by processing the test plastic film into a bag, and measuring a mass $m_f$ [kg] of the test film bag alone and a total surface area A [m²] associated with gas transmission in advance;

sealing the gas X into the test film bag at a density $\rho_x$, and measuring masses $m_0$ [kg], $m_1$ [kg], and $m_2$ [kg] of the test film bag in which the gas is sealed at least at times $t_0$ [s], $t_1$ [s], and $t_2$ [s] in an airtight vessel which is filled with the gas Y at a density $\rho_y$ so as to set a pressure P [Pa] equal to an internal pressure of the test film bag and in which a temperature is kept constant at a measurement temperature T [K];

obtaining volumes $V_{x0}$, $V_{x1}$, and $V_{x2}$ of the gas X in the test film bag at times $t_0$, $t_1$, and $t_2$ from $$V_{x0}=(m_0-m_f)/(\rho_x-\rho_y)$$

$$V_{x1}=(m_1-m_f)/(\rho_x-\rho_y)$$

$$V_{x2}=(m_2-m_f)/(\rho_x-\rho_y)$$

obtaining $\lambda_x$ by substituting the obtained results into the following equation for obtaining $\lambda_x$:

$$\lambda_x=\{a(t_1-t_0)-b(t_2-t_0)\}/(aV_{x1}-bV_{x2}-cV_{x0})$$

for $$a=\log V_{x0}-\log V_{x2}$$

$$b=\log V_{x0}-\log V_{x1}$$

$$c=\log V_{x1}-\log V_{x2}$$

and
computing $$k_x=-1/(\lambda_x RTA)$$

where R is a gas constant
thereby approximating the transmission rate $k_x$ of the gas X when the transmission rate $k_y$ ($k_x \gg k_y$) is known.

5. A method of measuring a gas transmission rate of a plastic film, in which when a transmission rate (a value representing the number of moles of a gas transmitted through a test piece with a unit area in a unit time at a unit partial pressure difference) $k_y$ [mol/m²sPa] of a gas Y is known, a transmission rate $k_x$ [mol/m²sPa] of a gas X through a test plastic film ($k_x \gg k_y$) is measured, comprising:

preparing a test film bag by processing the test plastic film into a bag, and measuring a mass $m_f$ [kg] of the test film bag alone and a total surface area A [m²] associated with gas transmission in advance;

sealing the gas X into the test film bag at a density $\rho_x$, and measuring masses $m_0$ [kg] and $m_1$ [kg] of the test film bag in which the gas is sealed at least at times $t_0$ [s] and $t_1$ [s] in an airtight vessel which is filled with the gas Y at a density $\rho_y$ so as to set a pressure P [Pa] equal to an internal pressure of the test film bag and in which a temperature is kept constant at a measurement temperature T [K];

obtaining volumes $V_{x0}$ and $V_{x1}$ of the gas X in the test film bag at times $t_o$ and $t_1$ from $$V_{x0}=(m_0-m_f)/(\rho_x-\rho_y)$$

$$V_{x1}=(m_1-m_f)/(\rho_x-\rho_y)$$

and
computing $$k_x=(V_{x1}-V_{x0})/\{(t_1-t_0)RTA\}$$

where R is a gas constant
thereby approximating the transmission rate $k_x$ of the gas X when the transmission rate $k_y$ ($k_x \gg k_y$) is known.

6. A method of measuring a gas transmission rate of a plastic film, which measures a transmission rate (a value representing the number of moles of a gas transmitted through a test piece with a unit area in a unit time at a unit partial pressure difference) $k_x$ [mol/m²sPa] of a gas X and a transmission rate $k_y$ [mol/m²sPa] of a gas Y through a test plastic film, comprising:

preparing first and second test film bags each obtained by processing the test plastic film into a bag, and measuring masses $m_f$ [kg] and $m_f'$ [kg] of the respective test film bags alone and total surface areas A [m²] and A' [m²] associated with gas transmission in advance;

sealing the gas X into the first test film bag at a density $\rho_x$, and measuring masses $m_0$ [kg], $m_1$ [kg], and $m_2$ [kg] of the first test film bag in which the gas is sealed at least at times $t_0$ [s], $t_1$ [s], and $t_2$ [s] in an airtight vessel which is filled with the gas Y at a density $\rho_y$ so as to set a pressure P [Pa] equal to an internal pressure of the first test film bag and in which a temperature is kept constant at a measurement temperature T [K];

sealing the gas Y into the second test film bag at a density $\rho_y'$, and measuring masses mol [kg], $m_1'$ [kg], and $m_2'$ [kg] of the second test film bag in which the gas is sealed at least at times $t_0'$ [s], $t_1'$ [s], and $t_2'$ [s] in an airtight vessel which is filled with the gas X at a density $\rho_x'$ so as to set a pressure P' [Pa] equal to an internal pressure of the second test film bag and in which a temperature is kept constant at a measurement temperature T' (T'=T) [K];

obtaining volumes $V_{x0}$, $V_{x1}$, and $V_{x2}$ of the gas X in the first test film bag at times $t_0$, $t_1$, and $t_2$ from $$V_{x0}=(m_0-m_f)/(\rho_x-\rho_y)$$

$$V_{x1}=(m_1-m_f)/(\rho_x-\rho_y)$$

$$V_{x2}=(m_2-m_f)/(\rho_x-\rho_y)$$

obtaining $\lambda_x$ by substituting the obtained results into the following equation for obtaining $\lambda_x$:

$$\lambda_x=\{a(t_1-t_0)-b(t_2-t_0)\}/(aV_{x1}-bV_{x2}-cV_{x0})$$

for $$a=\log V_{x0}-\log V_{x2}$$

$$b=\log V_{x0}-\log V_{x1}$$

$$c=\log V_{x1}-\log V_{x2}$$

obtaining volumes $V_{y0}'$, $V_{y1}'$, and $V_{y2}'$ of the gas Y in the second test film bag at times $t_0'$, $t_1'$, and $t_2'$ from $$V_{y0}'=(m_0'-m_f')/(\rho_y'-\rho_x')$$

$$V_{y1}'=(m_1'-m_f')/(\rho_y'-\rho_x')$$

$$V_{y2}'=(m_2'-m_f')/(\rho_y'-\rho_x')$$

obtaining $\lambda_y$ by substituting the obtained results into the following equation for obtaining $\lambda_y$:

$$\lambda_y=\{a'(t_1'-t_0')-b'(t_2'-t_0')\}/(a'V_{y1}'-b'V_{y2}'-c'V_{y0}')$$

for $$a'=\log V_{y0}'-\log V_{y2}'$$

$$b'=\log V_{y0}'-\log V_{y1}'$$

$$c'=\log V_{y1}'-\log V_{y2}'$$

when $\lambda_x>0$ and $\lambda_y<0$, computing $$k_x=-1/(\lambda_x RTA)+1/\{RT(-\lambda_x\lambda_y AA')^{1/2}\}$$

$$k_y=-1/(\lambda_y RTA')-1/\{RT(-\lambda_x\lambda_y AA')^{1/2}\}$$

where R is a gas constant
and
when $\lambda_x<0$ and $\lambda_y>0$, computing $$k_x=-1/(\lambda_x RTA)-1/\{RT(-\lambda_x\lambda_y AA')^{1/2}\}$$

$$k_y=-1/(\lambda_y RTA')+1/\{RT(-\lambda_x\lambda_y AA')^{1/2}\}$$

thereby obtaining the transmission rate $k_x$ of the gas X and the transmission rate $k_y$ of the gas Y.

7. A method according to any one of claims 1 to 6, wherein when a saturation vapor pressure of the gas X is lower than atmospheric pressure, the pressure in the airtight vessel is reduced to make a saturation vapor pressure in the test film bag become higher than the pressure in the airtight vessel.

8. A method of measuring a gas transmission rate of a plastic film, which measures a transmission rate (a value representing the number of moles of a gas transmitted through a test piece with a unit area in a unit time at a unit partial pressure difference) $k_x$ of a gas X, through a test plastic film, whose saturation vapor pressure is lower than atmospheric pressure at room temperature, comprising:

preparing a test film bag by processing the test plastic film into a bag, and measuring a mass $m_f$ [kg] of the test film bag alone and a total surface area A [m²] associated with as transmission in advance;

sealing the gas X into the test film bag while part of the gas is a liquid such that the vapor pressure is set in a saturated state, and allowing measurement of a mass of the test film bag in which the gas is sealed in an airtight vessel which is filled with a gas Y whose saturation vapor pressure is higher than atmospheric pressure at room temperature and in which a measurement temperature can be arbitrarily controlled;

measuring a mass $m_0$ [kg] of the test film bag in which the gas is sealed in state 0 in which an internal temperature of the airtight vessel is set to $T_0$ [K] and a pressure is set to $P_0$ [Pa] equal to atmospheric pressure (a saturation vapor pressure $P_{x0}$ [Pa] of the gas X, a density $\rho_x$ of the gas X, and a density $\rho_y$ of the gas Y);

measuring a mass $m_1$ [kg] of the test film bag in which the gas is sealed in state 1 in which an internal temperature of the airtight vessel is set to $T_1$ [K] (a pressure $P_1$ [Pa], a saturation vapor pressure $P_{x1}$ [Pa] of the gas X, a density $\rho_{x1}$ of the gas X, and a density $\rho_{y1}$ of the gas Y);

measuring a mass $m_2$ [kg] of the test film bag in which the gas is sealed in state 2 after a lapse of a predetermined period of time t [s] since state 1 while the internal temperature $T_1$ [K] of the airtight vessel (the pressure $P_1$ [Pa], the saturation vapor pressure $P_{x1}$ [Pa] of the gas X, the density $\rho_{x1}$ of the gas X, and the density $\rho_{y1}$ of the gas Y) is maintained;

after measurement in state 2, measuring a mass $m_3$ [kg] of the test film bag in which the gas is sealed in state 3 in which the internal temperature of the airtight vessel is set to $T_3$ [K] (a pressure $P_3$ [Pa] and a saturation vapor pressure $P_{x3}$ [Pa]);

obtaining a total mass of the liquid and gas in the test film bag in state 1 from $$m_{x1}+\rho_{x1}V_{x1}=m_1-m_f+(m_0-m_1)(P_0/P_{x0}-1)/(P_0/P_{x0}-P_1/P_{x1})$$

obtaining the total mass of the liquid and gas in the test film bag in state 2 from $$m_{x2}+\rho_{x2}V_{x2}=m_3-m_f+(m_2-m_3)(P_1/P_{x2}-1)/(P_1/P_{x2}-P_3/P_{x3})$$

and obtaining the transmission rate $k_x$ of the gas X by substituting the computation results into the following equation and computing the equation:

$$k_x=\{(m_{x1}+\rho_{x1}V_{x1})-(m_{x2}+\rho_{x2}V_{x2})\}/(tP_xA).$$

9. A method according to any one of claims 1 to 6 and 8, wherein in measurement of the mass, a measured weight value is corrected on the basis of a gravitational acceleration at a measurement place.

10. A measuring apparatus used to execute the method of measuring a gas transmission rate of a plastic film which is defined in any one of claims 1 to 6 and 8, comprising:

a constant temperature vessel which is used as the airtight vessel and includes internal temperature control means and gas filling means;

an electronic balance which is mounted in the constant temperature vessel and measures a mass of a test film bag in which the gas is sealed; and an arithmetic processing unit in which an arithmetic processing program defined in any one of claims 1 to 6 and 8 is installed in advance and which obtains a transmission rate value of a test gas by inputting the measurement results.

11. An apparatus according to claim 10, further comprising measurement automating means for acquiring a measured mass value at a predetermined time from the electronic balance by setting an internal temperature in the constant temperature vessel to a measurement temperature through the internal temperature control means.

12. A computer program product storing program instructions which cause a computer to execute arithmetic processing for obtaining a transmission rate (a value representing the number of moles of a gas transmitted through a test piece with a unit area in a unit time at a unit partial pressure difference) $k_y$ [mol/m²sPa] of a gas Y through a test plastic film when a transmission rate $k_x$ [mol/m²sPa] of a gas X is known, the program instructions comprising:

registering measurement results on a mass $m_f$ [kg] of a test film bag alone, which is obtained by processing the test plastic film into a bag, and a total surface area A [m²] associated with gas transmission;

registering results obtained by sealing the gas X into the test film bag at a density $\rho_x$, and measuring masses $m_0$ [kg], $m_1$ [kg], and $m_2$ [kg] of the test film bag in which the gas is sealed at least at times $t_0$ [s], $t_1$ [s], and $t_2$ [s] in an airtight vessel which is filled with the gas Y at a density $\rho_y$ so as to set a pressure P [Pa] equal to an internal pressure of the test film bag and in which a temperature is kept constant at a measurement temperature T [K];

obtaining volumes $V_{x0}$, $V_{x1}$, and $V_{x2}$ of the gas X in the test film bag at times $t_0$, $t_1$, and $t_2$ from (S13)

$$V_{x0}=(m_0-m_f)/(\rho_x-\rho_y)$$

$$V_{x1}=(m_1-m_f)/(\rho_x-\rho_y)$$

$$V_{x2}=(m_2-m_f)/(\rho_x-\rho_y)$$

obtaining $\lambda_x$ by substituting the obtained results into the following equation for obtaining $\lambda_x$ (S14):

$$\lambda_x\{a(t_1-t_0)-b(t_2-t_0)\}/(aV_{x1}-bV_{x2}-cV_{x0})$$

for $a=\log V_{x0}-\log V_{x2}$ $b=\log V_{x0}-\log V_{x1}$ $c=\log V_{x1}-\log V_{x2}$ and computing $$k_y=(\lambda_x K_x^2+K_x)/(RTA)$$

where R is a gas constant and $K_x=k_xRTA$ thereby obtaining the transmission rate $k_y$ of the gas Y when the transmission rate $k_x$ is known.

13. A computer program product storing program instructions which cause a computer to execute arithmetic processing for obtaining a transmission rate (a value representing the number of moles of a gas transmitted through a test piece with a unit area in a unit time at a unit partial pressure difference) $k_x$ [mol/m²sPa] of a gas X through a test plastic film when a transmission rate $k_y$ [mol/m²sPa] of a gas Y is known, the program instructions comprising:

registering measurement results on a mass $m_f$ [kg] of a test film bag alone, which is obtained by processing the test plastic film into a bag, and a total surface area A [m²] associated with gas transmission;

registering results obtained by sealing the gas X into the test film bag at a density $\rho_x$, and measuring masses $m_0$ [kg], $m_1$ [kg], and $m_2$ [kg] of the test film bag in which the gas is sealed at least at times $t_0$ [s], $t_1$ [s], and $t_2$ [s] in an airtight vessel which is filled with the gas Y at a density $\rho_y$ so as to set a pressure P [Pa] equal to an internal pressure of the test film bag and in which a temperature is kept constant at a measurement temperature T [K];

obtaining volumes $V_{x0}$, $V_{x1}$, and $V_{x2}$ of the gas X in the test film bag at times $t_0$, $t_1$, and $t_2$ from $$V_{x0}=(m_0-m_f)/(\rho_x-\rho_y)$$

$$V_{x1}=(m_1-m_f)/(\rho_x-\rho_y)$$

$$V_{x2}=(m_2-m_f)/(\rho_x-\rho_y)$$

obtaining $\lambda_x$ by substituting the obtained results into the following equation for obtaining $\lambda_x$:

$$\lambda_x=\{a(t_1-t_0)-b(t_2-t_0)\}/(aV_{x1}-bV_{x2}-cV_{x0})$$

for $a=\log V_{x0}-\log V_{x2}$ $b=\log V_{x0}-\log V_{x1}$ $c=\log V_{x1}-\log V_{x2}$ and when $\lambda_x > 0$, computing $$k_x = \{-1 + (1 + 4\lambda_x K_y)^{1/2}\}/(2\lambda_x RTA)$$

where R is a gas constant and $K_x = k_x RTA$ and when $\lambda_x < 0$, computing $$k_x = \{-1 \pm (1 + 4\lambda_x K_y)^{1/2}\}/(2\lambda_x RTA)$$

thereby obtaining the transmission rate $k_x$ of the gas X when the transmission rate $k_y$ is known.

14. A computer program product storing program instructions which cause a computer to execute arithmetic processing for obtaining a transmission rate (a value representing the number of moles of a gas transmitted through a test piece with a unit area in a unit time at a unit partial pressure difference) $k_x$ [mol/m$^2$sPa] of a gas X through a test plastic film when a transmission rate $k_y$ [mol/m$^2$sPa] of a gas Y is known, the program instructions comprising:

registering measurement results on a mass $m_f$[kg] of a test film bag alone, which is obtained by processing the test plastic film into a bag, and a total surface area A [m$^2$] associated with gas transmission;

registering results obtained by sealing the gas X into the test film bag at a density $\rho_x$, and measuring masses $m_0$ [kg], $m_1$ [kg], and $m_2$ [kg] of the test film bag in which the gas is sealed at least at times $t_0$ [s], $t_1$ [s], and $t_2$ [s] in an airtight vessel which is filled with the gas Y at a density $\rho_y$ so as to set a pressure P [Pa] equal to an internal pressure of the test film bag and in which a temperature is kept constant at a measurement temperature T [K];

obtaining volumes $V_{x0}$, $V_{x1}$, and $V_{x2}$ of the gas X in the test film bag at times $t_0$, $t_1$, and $t_2$ from $$V_{x0} = (m_0 - m_f)/(\rho_x - \rho_y)$$

$$V_{x1} = (m_1 - m_f)/(\rho_x - \rho_y)$$

$$V_{x2} = (m_2 - m_f)/(\rho_x - \rho_y)$$

obtaining $\lambda_x$ by substituting the obtained results into the following equation for obtaining $\lambda_x$:

$$\lambda_x = \{a(t_1 - t_0) - b(t_2 - t_0)\}/(aV_{x1} - bV_{x2} - cVx_0)$$

for $$a = \log V_{x0} - \log V_{x2}$$

$$b = \log V_{x0} - \log V_{x1}$$

$$c = \log V_{x1} - \log V_{x2}$$

and computing $$k_x = -1/(\lambda_x RTA)$$

where R is a gas constant
thereby approximating the transmission rate $k_x$ of the gas X when the transmission rate $k_y$ is known.

15. A computer program product storing program instructions which cause a computer to execute arithmetic processing for obtaining a transmission rate (a value representing the number of moles of a gas transmitted through a test piece with a unit area in a unit time at a unit partial pressure difference) $k_x$ [mol/m$^2$sPa] of a gas X through a test plastic film when a transmission rate $k_y$ [mol/m$^2$sPa] of a gas Y is known, the program instructions comprising:

registering measurement results on a mass $m_f$[kg] of a test film bag alone, which is obtained by processing the test plastic film into a bag, and a total surface area A [m$^2$] associated with gas transmission;

registering results obtained by sealing the gas X into the test film bag at a density $\rho_x$, and measuring masses $m_0$ [kg] and $m_1$ [kg] of the test film bag in which the gas is sealed at least at times $t_0$ [s] and $t_1$ [s] in an airtight vessel which is filled with the gas Y at a density $\rho_y$ so as to set a pressure P [Pa] equal to an internal pressure of the test film bag and in which a temperature is kept constant at a measurement temperature T [K];

obtaining volumes $V_{x0}$ and $V_{x1}$ of the gas X in the test film bag at times $t_0$ and $t_1$ from $$V_{x0} = (m_0 - m_f)/(\rho_x - \rho_y)$$

$$V_{x1} = (m_1 - m_f)/(\rho_x - \rho_y)$$

and computing $$k_x = (V_{x1} - V_{x0})/\{(t_1 - t_0)RTA\}$$

where R is a gas constant
thereby approximating the transmission rate $k_x$ of the gas X when the transmission rate $k_y$ ($k_x \gg k_y$) is known.

16. A computer program product storing program instructions which cause a computer to execute arithmetic processing for obtaining a transmission rate (a value representing the number of moles of a gas transmitted through a test piece with a unit area in a unit time at a unit partial pressure difference) $k_x$ [mol/m$^2$sPa] of a gas X and a transmission rate $k_y$ [mol/m$^2$sPa] of a gas Y through a test plastic film, the program instructions comprising:

registering measurement results on masses $m_f$[kg] and $m_f'$ [kg] of first and second test film bags alone, each of which is obtained by processing the test plastic film into a bag, and total surface areas A [m$^2$] and A' [m$^2$] associated with gas transmission;

registering results obtained by sealing the gas X into the first test film bag at a density $\rho_{x1}$, and measuring masses $m_0$ [kg], $m_1$ [kg], and $m_2$ [kg] of the first test film bag in which the gas is sealed at least at times $t_0$ [s], $t_1$ [s], and $t_2$ [s] in an airtight vessel which is filled with the gas Y at a density $\rho_y$ so as to set a pressure P [Pa] equal to an internal pressure of the first test film bag and in which a temperature is kept constant at a measurement temperature T [K];

registering results obtained by sealing the gas Y into the second test film bag at a density $\rho_y'$, and measuring masses $m_0'$ [kg], $m_1'$ [kg], and $m_2'$ [kg] of the second test film bag in which the gas is sealed at least at times $t_0'$ [s], $t_1'$ [s], and $t_2'$ [s] in an airtight vessel which is filled with the gas X at a density $\rho_x'$ so as to set a pressure P' [Pa] equal to an internal pressure of the second test film bag and in which a temperature is kept constant at a measurement temperature T' (T'=T) [K];

obtaining volumes $V_{x0}$, $V_{x1}$, and $V_{x2}$ of the gas X in the first test film bag at times $t_0$, $t_1$, and $t_2$ from $$V_{x0} = (m_0 - m_f)/(\rho_x - \rho_y)$$

$$V_{x1} = (m_1 - m_f)/(\rho_x - \rho_y)$$

$$V_{x2} = (m_2 - m_f)/(\rho_x - \rho_y)$$

obtaining $\lambda_x$ by substituting the obtained results into the following equation for obtaining $\lambda_x$:

$$\lambda_x = \{a(t_1-t_0)-b(t_2-t_0)\}/(aV_{x1}-bV_{x2}-cV_{x0})$$

for $$a = \log V_{x0} - \log V_{x2}$$

$$b = \log V_{x0} - \log V_{x1}$$

$$c = \log V_{x1} - \log V_{x2}$$

obtaining volumes $V_{y0}'$, $V_{y1}'$, and $V_{y2}'$ of the gas Y in the second test film bag at times $t_0'$, $t_1'$, and $t_2'$ from $$V_{y0}' = (m_0'-m_f')/(\rho_y'-\rho_x')$$

$$V_{y1}' = (m_1'-m_f')/(\rho_y'-\rho_x')$$

$$V_{y2}' = (m_2'-m_f')/(\rho_y'-\rho_x')$$

obtaining $\lambda_y$ by substituting the obtained results into the following equation for obtaining $\lambda_y$:

$$\lambda_y = \{a'(t_1'-t_0')-b'(t_2'-t_0')\}/(a'V_{y1}'-b'V_{y2}'-c'V_{y0}')$$

for $$a' = \log V_{y0}' - \log V_{y2}'$$

$$b' = \log V_{y0}' - \log V_{y1}'$$

$$c' = \log V_{y1}' - \log V_{y2}'$$

when $\lambda_x > 0$ and $\lambda_y < 0$, computing $$k_x = -1/(\lambda_x RTA) + 1/\{RT(-\lambda_x\lambda_y AA')^{1/2}\}$$

$$k_y = -1/(\lambda_y RTA') - 1/\{RT(-\lambda_x\lambda_y AA')^{1/2}\}$$

where R is a gas constant
and
when $\lambda_x < 0$ and $\lambda_y > 0$, computing $$k_x = -1/(\lambda_x RTA) - 1/\{RT(-\lambda_x\lambda_y AA')^{1/2}\}$$

$$k_y = -1/(\pi_y RTA') + 1/\{RT(-\lambda_x\lambda_y AA')^{1/2}\}$$

thereby obtaining the transmission rate $k_x$ of the gas X and the transmission rate $k_y$ of the gas Y.

17. A computer program product storing program instructions which cause a computer to execute arithmetic processing for obtaining a transmission rate (a value representing the number of moles of a gas transmitted through a test piece with a unit area in a unit time at a unit partial pressure difference) $k_x$ of a gas X, through a test plastic film, whose saturation vapor pressure is lower than atmospheric pressure at room temperature, the program instructions comprising:

registering measurement results on a mass $m_f$ [kg] of a test film bag alone, which is obtained by processing the test plastic film into a bag, and a total surface area A [m²] associated with gas transmission;

registering measurement results in states 0 to 3 which are obtained by sealing the gas X into the test film bag while part of the gas is a liquid such that the vapor pressure is set in a saturated state, and allowing measurement of a mass of the test film bag in which the gas is sealed in an airtight vessel which is filled with a gas Y whose saturation vapor pressure is higher than atmospheric pressure at room temperature and in which a measurement temperature can be arbitrarily controlled, state 0: setting an internal temperature of the airtight vessel to $T_0$ [K] and a pressure to $P_0$ [Pa] equal to atmospheric pressure (a saturation vapor pressure $P_{x0}$ [Pa] of the gas X, a density $\rho_x$ of the gas X, and a density $\rho_y$ of the gas Y) and measuring a mass $m_0$ [kg] of the test film bag in which the gas is sealed, state 1: setting the internal temperature of the airtight vessel is set to $T_1$ [K] (a pressure $P_1$ [Pa], a saturation vapor pressure $P_{x1}$ [Pa] of the gas X, a density $\rho_{x1}$ of the gas X, and a density $\rho_{y1}$ of the gas Y) and measuring a mass $m_1$ [kg] of the test film bag in which the gas is sealed, state 2: measuring a mass $m_2$ [kg] of the test film bag in which the gas is sealed after a lapse of a predetermined period of Time t [s] since state 1 while the internal temperature $T_1$ [K] of the airtight vessel (the pressure $P_1$ [Pa], the saturation vapor pressure $P_{x1}$ [Pa] of the gas X, the density $\rho_{x1}$ of the gas X, and the density $\rho_{y1}$ of the gas Y) is maintained, and state 3: after measurement in state 2, setting the internal temperature of the airtight vessel to $T_3$ [K] (a pressure $P_3$ [Pa] and a saturation vapor pressure $P_{x3}$ [Pa]) and measuring a mass $m_3$ [kg] of the test film bag in which the gas is sealed;

obtaining a total mass of the liquid and gas in the test film bag in state 1 from $$m_{x1}+\rho_{x1}V_{x1}=m_1-m_f+(m_0-m_1)(P_0/P_{x0}<1)/(P_0/P_{x0}-P_1/P_{x1})$$

obtaining the total mass of the liquid and gas in the test film bag in state 2 from $$m_{x2}+\rho_{x2}V_{x2}=m_3-m_f+(m_2-m_3)(P_1/P_{x2}-1)/(P_1/P_{x2}-P_3/P_{x3})$$

and obtaining the transmission rate $k_x$ of the gas X by substituting the computation results into the following equation and computing the equation:

$$k_x = \{(m_{x1}+\rho_{x1}V_{x1})-(m_{x2}+\rho_{x2}Vx2)\}/(tP_xA)$$

18. A product according to any one of claims 12 to 17, further comprising: correcting a weight measurement result on the basis of a gravitational acceleration at a measurement place to measure the mass.

* * * * *